(12) United States Patent
Ariyoshi

(10) Patent No.: US 8,180,573 B2
(45) Date of Patent: May 15, 2012

(54) SAMPLE PROCESSING APPARATUS, METHOD OF OUTPUTTING PROCESSING RESULT BY SAMPLE PROCESSING APPARATUS, AND COMPUTER PROGRAM PRODUCT

(75) Inventor: Shunsuke Ariyoshi, Kobe (JP)

(73) Assignee: Sysmex Corporation, Kobe (JP)

( * ) Notice: Subject to any disclaimer, the term of this patent is extended or adjusted under 35 U.S.C. 154(b) by 200 days.

(21) Appl. No.: 12/321,658

(22) Filed: Jan. 22, 2009

(65) Prior Publication Data

US 2009/0187348 A1 Jul. 23, 2009

(30) Foreign Application Priority Data

Jan. 23, 2008 (JP) ................................ 2008-012463

(51) Int. Cl.
*G01N 33/48* (2006.01)
(52) U.S. Cl. ................ 702/19; 702/27; 422/67
(58) Field of Classification Search ............ 702/19, 702/27
See application file for complete search history.

(56) References Cited

U.S. PATENT DOCUMENTS

| | | | | |
|---|---|---|---|---|
| 4,764,342 A * | 8/1988 | Kelln et al. | ...................... | 422/72 |
| 4,971,913 A * | 11/1990 | Manabe et al. | .................. | 436/55 |
| 5,242,803 A * | 9/1993 | Burtis et al. | .................. | 435/7.92 |
| 5,420,408 A * | 5/1995 | Weyrauch et al. | ............. | 235/454 |
| 5,676,673 A * | 10/1997 | Ferre et al. | ..................... | 606/130 |
| 5,719,059 A * | 2/1998 | Mimura et al. | .................. | 436/50 |
| 5,730,939 A * | 3/1998 | Kurumada et al. | ............. | 422/67 |
| 5,773,662 A * | 6/1998 | Imai et al. | ......................... | 436/50 |
| 5,854,075 A * | 12/1998 | Levine et al. | ................... | 436/46 |
| 6,030,630 A * | 2/2000 | Fleury et al. | ................... | 424/401 |
| 6,509,192 B1 * | 1/2003 | Young | .............................. | 436/10 |
| 6,579,717 B1 * | 6/2003 | Matsubara et al. | ............. | 436/50 |
| 7,029,922 B2 * | 4/2006 | Miller | ............................ | 436/180 |
| 7,229,592 B2 * | 6/2007 | Devlin et al. | .................... | 422/67 |
| 7,250,303 B2 * | 7/2007 | Jakubowicz et al. | ........... | 436/54 |
| 2001/0051952 A1 * | 12/2001 | Nakazato | .................... | 707/104.1 |
| 2002/0076352 A1 * | 6/2002 | Motegi et al. | .................... | 422/64 |
| 2004/0102997 A1 * | 5/2004 | Kikuchi et al. | .................... | 705/1 |
| 2004/0149015 A1 * | 8/2004 | Hansen et al. | ..................... | 73/40 |
| 2006/0008384 A1 * | 1/2006 | Devlin et al. | .................... | 422/64 |
| 2006/0178838 A1 * | 8/2006 | Adelson et al. | ................. | 702/19 |
| 2006/0210438 A1 | 9/2006 | Nagai et al. | | |
| 2006/0265133 A1 * | 11/2006 | Cocks et al. | .................... | 702/19 |
| 2008/0063570 A1 * | 3/2008 | Fujino et al. | ..................... | 422/99 |

* cited by examiner

*Primary Examiner* — Drew A Dunn
*Assistant Examiner* — Timothy H Hwang
(74) *Attorney, Agent, or Firm* — Brinks Hofer Gilson & Lione

(57) ABSTRACT

Disclosed is a sample processing apparatus, comprising: a sample processing unit for processing a sample with an auxiliary item used to process the sample; an output device for outputting a processing result by the sample processing unit; and a controller for determining whether or not the auxiliary item is appropriate for the sample processing by sample processing unit, and controlling, when determining that the auxiliary item is not appropriate for the sample processing by the sample processing unit, the output device so as to output the processing result and reliability information showing that the processing result has a low reliability. Also disclosed is a method for outputting the processing result by the sample processing apparatus and a computer program product.

20 Claims, 32 Drawing Sheets

FIG. 19

Database storing relation between measurement item and reagent used

| Measurement item | Reagent used |
|---|---|
| WBC | STOMATOLYSER-FB(II), CELLPACK (II) |
| RBC | SE sheath (II), CELLPACK (II) |
| HGB | SULFOLYSER, CELLPACK (II) |
| HCT | SE sheath (II), CELLPACK (II) |
| MCV | SE sheath (II), CELLPACK (II) |
| MCHC | SE sheath (II), SULFOLYSER, CELLPACK (II) |
| PLT | SE sheath (II), CELLPACK (II) |
| NEUT | STOMATOLYSER-4DL, STOMATOLYSER-4DS, CELLPACK (II) |
| LYMPH | STOMATOLYSER-4DL, STOMATOLYSER-4DS, CELLPACK (II) |
| MONO | STOMATOLYSER-4DL, STOMATOLYSER-4DS, CELLPACK (II) |
| EO | STOMATOLYSER-4DL, STOMATOLYSER-4DS, CELLPACK (II) |
| BASO | STOMATOLYSER-FB(II), CELLPACK (II) |

| Item | Data |
|---|---|
| WBC | 61.2 |
| RBC | 464 |
| HGB | 12.8 |
| HCT | 39.3 |
| MCV | 84.7 |
| MCH | 27.6 |
| MCHC | 32.6 |
| PLT | 20.4 |

FIG. 25

| Item | Data |
|---|---|
| WBC | 61.2 |
| RBC | 464 |
| HGB | 12.8 |
| HCT | 39.3 |
| MCV | 84.7 |
| MCH | 27.6 |
| MCHC | 32.6 |
| PLT | 20.4 |

FIG. 27

| | Lot No. | Expiration date |
|---|---|---|
| CELLPACK | 12345678 | 2010/01/23 |
| STOMATOLYSER 4DL | 12345678 | 2010/01/23 |
| STOMATOLYSER 4DS | (Unknown) | —/—/— |
| SULFOLYSER | 12345678 | 2010/01/23 |

IC5 ⚠ Values of NEUT, LYMPH, MONO, EO, and BASO are not guaranteed.

Main | Graph | Time series | Q-Flag | Service | Research | Reagent information

Not Validated

SC2, SC2e, SC2d

US 8,180,573 B2

SAMPLE PROCESSING APPARATUS, METHOD OF OUTPUTTING PROCESSING RESULT BY SAMPLE PROCESSING APPARATUS, AND COMPUTER PROGRAM PRODUCT

RELATED APPLICATIONS

This application claims priority under 35 U.S.C. §119 to Japanese Patent Application No. JP2008-012463 filed Jan. 23, 2008, the entire content of which is hereby incorporated by reference.

TECHNICAL FIELD

The present invention relates to a sample processing apparatus such as a hemocytometer or a smear preparing apparatus that uses an auxiliary item used to process a sample for processing the sample such as blood, a processing result output method by the sample processing apparatus, and a computer program product.

BACKGROUND ART

In hospitals and inspection agencies, a sample analyzer has been used to measure an item regarding the properties of a sample such as blood collected from a living organism (see U.S. Patent Publication No. 2006-210438 for example). The sample analyzer as described above has been generally recommended to be used with dedicated reagent (genuine product) specified by a supplier (maker). The reason is therefor that the dedicated reagent is optimized to provide an accurate analysis result by the repetition of evaluation experiments while any sample analysis using reagents other than the genuine product (not-genuine product) may not provide such an accurate analysis result to cause a reduced reliability in the analysis result. This reason also applies to a slide glass in a smear preparing apparatus for example. Specifically, the use of a not-genuine slide glass may cause breakage of a to-be-observed component in the sample, which declines the reliability to a prepared sample. When not-genuine stain solution is used in the smear preparing apparatus, blood cells may not be stained in a favorable manner, causing an adverse impact on the observation result.

However, there may be a case where a user does not know that the use of a not-genuine product causes a reduced reliability in the analysis result for example or a user does not know that the product used by the user is a not-genuine product. When a patient receives a medical care based on an analysis result having a reduced reliability for example, an adverse impact may be caused on the patient by an inappropriate treatment or medication.

SUMMARY OF INVENTION

The scope of the present invention is defined solely by the appended claims, and is not affected to any degree by the statements within this summary.

A first aspect of the present invention is a sample processing apparatus, comprising:
a sample processing unit for processing a sample with an auxiliary item used to process the sample;
an output device for outputting processing result by the sample processing unit; and
a controller for determining whether or not the auxiliary item is appropriate for sample processing by the sample processing unit, and controlling, when determining that the auxiliary item is not appropriate for the sample processing by the sample processing unit, the output device so as to output the processing result and reliability information showing that the processing result has a low reliability.

A second aspect of the present invention is a processing result output method by a sample processing apparatus, comprising:
processing a sample with using an auxiliary item;
acquiring a processing result of the sample processed using the auxiliary item;
determining whether or not the auxiliary item is appropriate for sample processing; and
outputting, when the auxiliary item is determined as inappropriate for the sample processing, the processing result and reliability information showing that the processing result has a low reliability.

A third aspect of the present invention is a computer program product, comprising:
a computer readable medium; and
instructions, on the computer readable medium, adapted to enable a general purpose computer to perform operations, comprising:
acquiring a result of a processing of a sample processed with an auxiliary item;
determining whether or not the auxiliary item is appropriate for sample processing; and
outputting, when the auxiliary item is determined as inappropriate for the sample processing, the processing result and reliability information showing that the processing result has a low reliability.

BRIEF DESCRIPTION OF DRAWINGS

FIG. 19 illustrates the contents of a database that is stored in the hemocytometer of FIG. 1 and that shows the relation between a measurement item and to-be-used genuine reagent;

FIG. 22 illustrates an example of an analysis result display screen displayed in the data processing apparatus of the hemocytometer of FIG. 1 when not-genuine reagent is used;

FIG. 23 illustrates a modification example of the analysis result display screen displayed in the data processing apparatus of the hemocytometer of FIG. 1 when not-genuine reagent is used;

FIG. 25 illustrates a modification example of the analysis result display screen displayed in the data processing apparatus of the hemocytometer of FIG. 1 when not-genuine reagent is used;

FIG. 27 illustrates the reagent information screen displayed in the data processing apparatus of the hemocytometer of FIG. 1;

DESCRIPTION OF EMBODIMENTS

The preferred embodiments of the present invention will be described hereinafter with reference to the drawings.

First Embodiment

Figure 1:
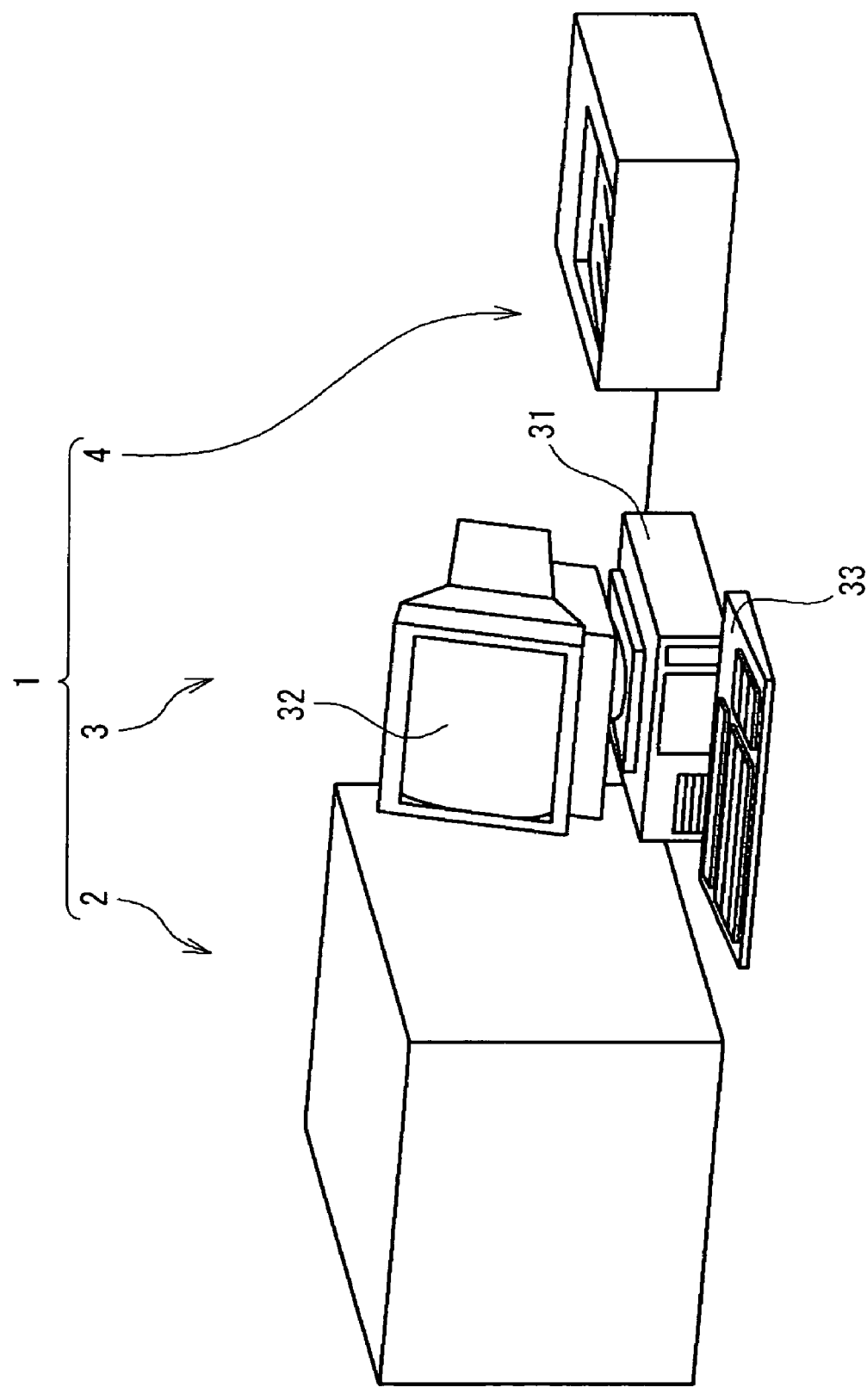
FIG. 1 is a perspective view illustrating a hemocytometer according to a first embodiment of the present invention.

FIG. 1 is a perspective view illustrating a hemocytometer that is a sample processing apparatus according to the first embodiment of the present invention. A hemocytometer 1 of this embodiment is composed of: a measurement section 2 that measures or counts blood cells; a data processing apparatus 3 that processes a measurement value outputted from the measurement section 2 to obtain an analysis result (processing result); and a printer 4 that prints the analysis result.

[Configuration of Measurement Section 2]

Figure 2:
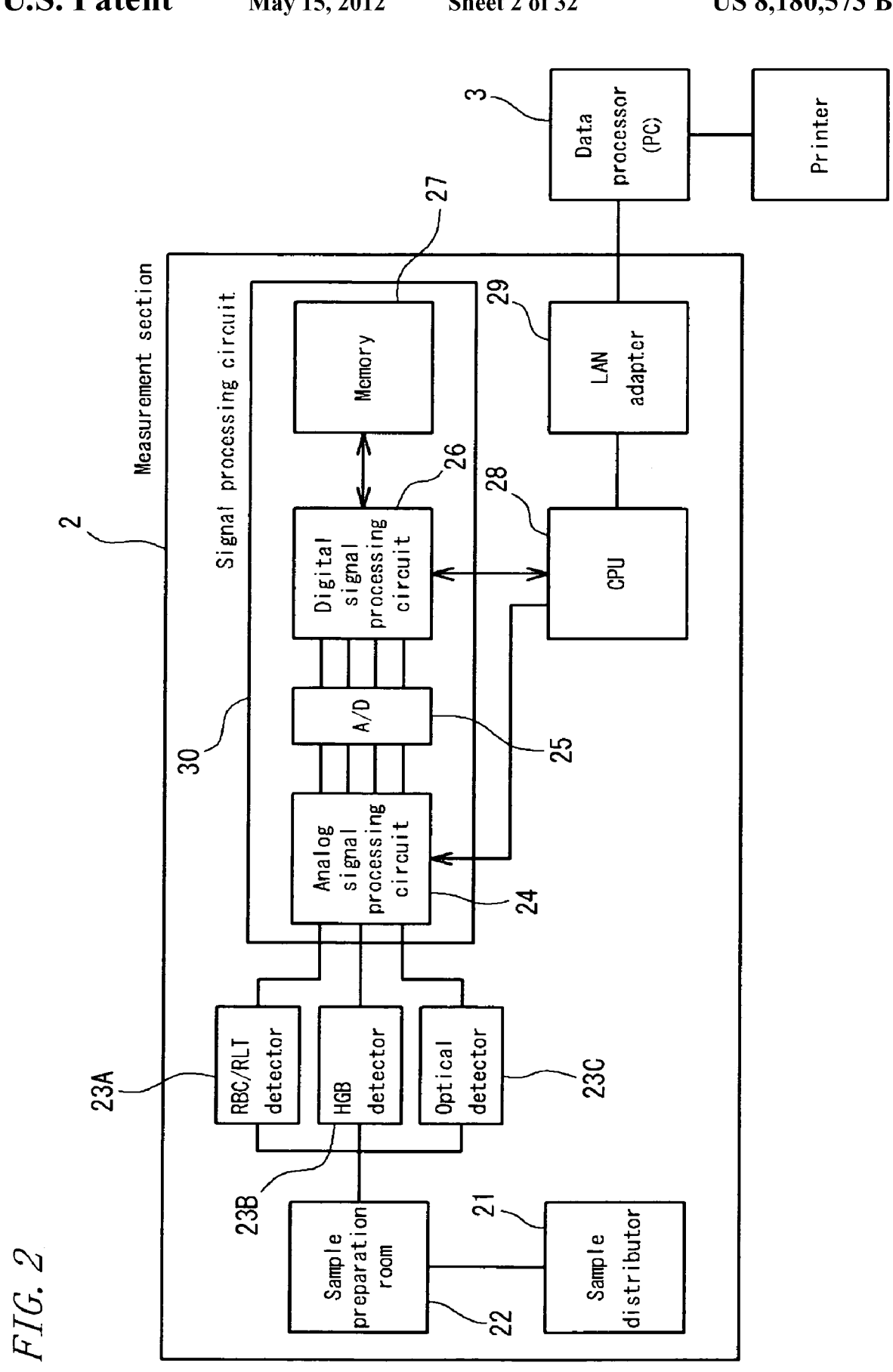
FIG. 2 is a block diagram illustrating the configuration of a measurement section in the hemocytometer of FIG. 1.

As shown in FIG. 2, the measurement section 2 includes: a sample distributor 21 that sucks the blood in a blood collection tube to distribute the blood; a sample preparation section 22 that prepares the distributed sample; a plurality of detectors 23A to 23C that measure samples; an analog signal processing circuit 24 that subjects the output from the detectors 23A to 23C to an amplification or filter processing for example; an A/D converter 25 that converts the output from the analog signal processing circuit 24 to a digital signal; and a digital signal processing circuit 26 that subjects the digital signal to a predetermined waveform processing.

The measurement section 2 also includes: a memory 27 connected to the digital signal processing circuit 26; a CPU 28 connected to the analog signal processing circuit 24 and the digital signal processing circuit 26; and a LAN adapter 29 connected to the CPU 28. The data processing apparatus 3 is connected to the measurement section 2 via the LAN adapter 29. The analog signal processing circuit 24, the A/D converter 25, the digital signal processing circuit 26, and the memory 27 constitute a signal processing circuit 30 to electric signals outputted from the detectors 23A to 23C.

The sample distributor 21 is configured to dispense a predetermined distribution amount of blood to the sample preparation section 22. The sample preparation section 22 is also configured to prepare a measurement sample out of the blood and reagent dispensed from the sample distributor 21 to supply the prepared measurement sample to the detectors 23A to 23C. The detectors 23A to 23C are composed of: an RBC/PLT detector 23A; an HGB detector 23B; and an optical detector 23C.

(Detailes of Measurement by RBC/PLT Detector 23A)

Figure 4:
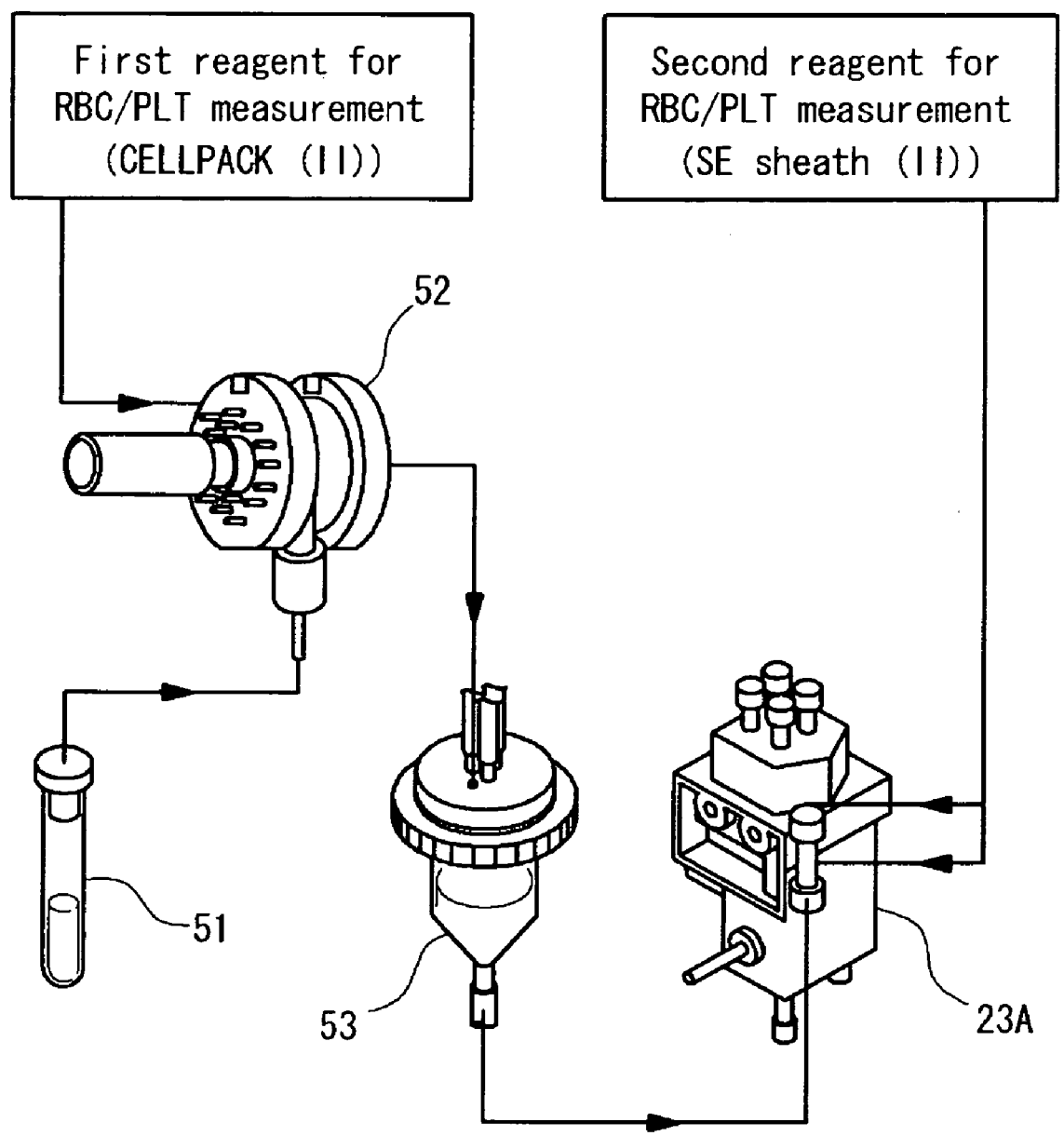
FIG. 4 illustrates the flow of an RBC/PLT measurement in the hemocytometer of FIG. 1.

The RBC/PLT detector 23A carries out the measurement of the number of red blood cells (RBC measurement) and the measurement of the number of platelets (PLT measurement). FIG. 4 illustrates the flow of the measurement by the RBC/PLT detector 23A. The blood in a blood collection tube 51 is sucked through a suction pipette to a sampling valve 52 and is quantitated in a predetermined amount by the sampling valve 52. The quantitated blood is diluted by the first reagent for the RBC/PLT measurement and the resultant diluted sample is sent to an RBC sample chamber 53. Thereafter, the diluted sample and the second reagent are sent to the RBC/PLT detector 23A and RBC and PLT are counted by the RBC/PLT detector 23A based on the sheath flow DC detection method. At the same time, an HCT (hematocrit value) is calculated based on the red-blood-cell pulse height detection method.

(Details of Measurement by HGB Detector 23B)

Figure 5:
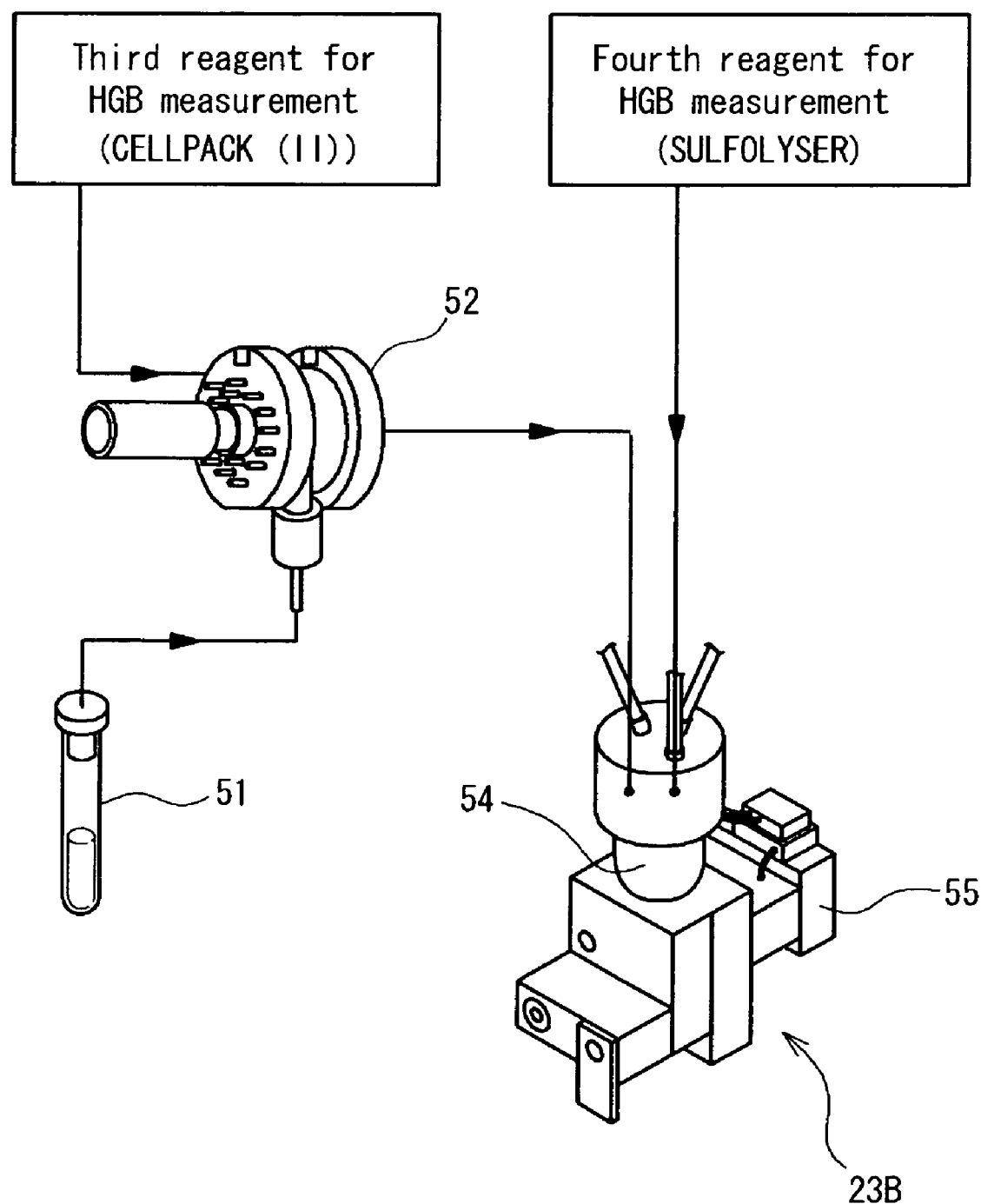
FIG. 5 illustrates the flow of an HGB measurement in the hemocytometer of FIG. 1.

The HGB detector 23B measures a hemoglobin content in blood (HGB measurement). FIG. 5 illustrates the flow of the measurement by the HGB detector 23B. The blood in the blood collection tube 51 is sucked through a suction pipette into the sampling valve 52 and is quantitated to a predetermined amount by the sampling valve 52. The quantitated blood is diluted by the third reagent for HGB measurement and the resultant diluted sample is sent to a flow cell 54 of the HGB detector 23B. At the same time, the fourth reagent for HGB measurement is added to the sample to further dilute the diluted sample by the fourth reagent. As a result, the red blood cells in this diluted sample are hemolyzed and hemoglobin is inverted to SLS-hemoglobin.

Then, the HGB detector 23B directs the light emitted from a light-emitting diode 55 toward the diluted sample through a lens and measures the concentration of the SLS-hemoglobin as an absorbance. Then, the HGB detector 23B compares the absorbance with the absorbance of the diluent measured in advance before the diluent is mixed with the sample, thereby performing the HGB measurement.

The RBC and HCT measured by the RBC/PLT detector 23A and the HGB measured by the HGB detector 23B are also used for the calculation of a mean corpuscular volume (MCV) and a mean corpuscular hemoglobin concentration (MCHC).

(Details of Measurement by Optical Detector 23C)

Figure 6:
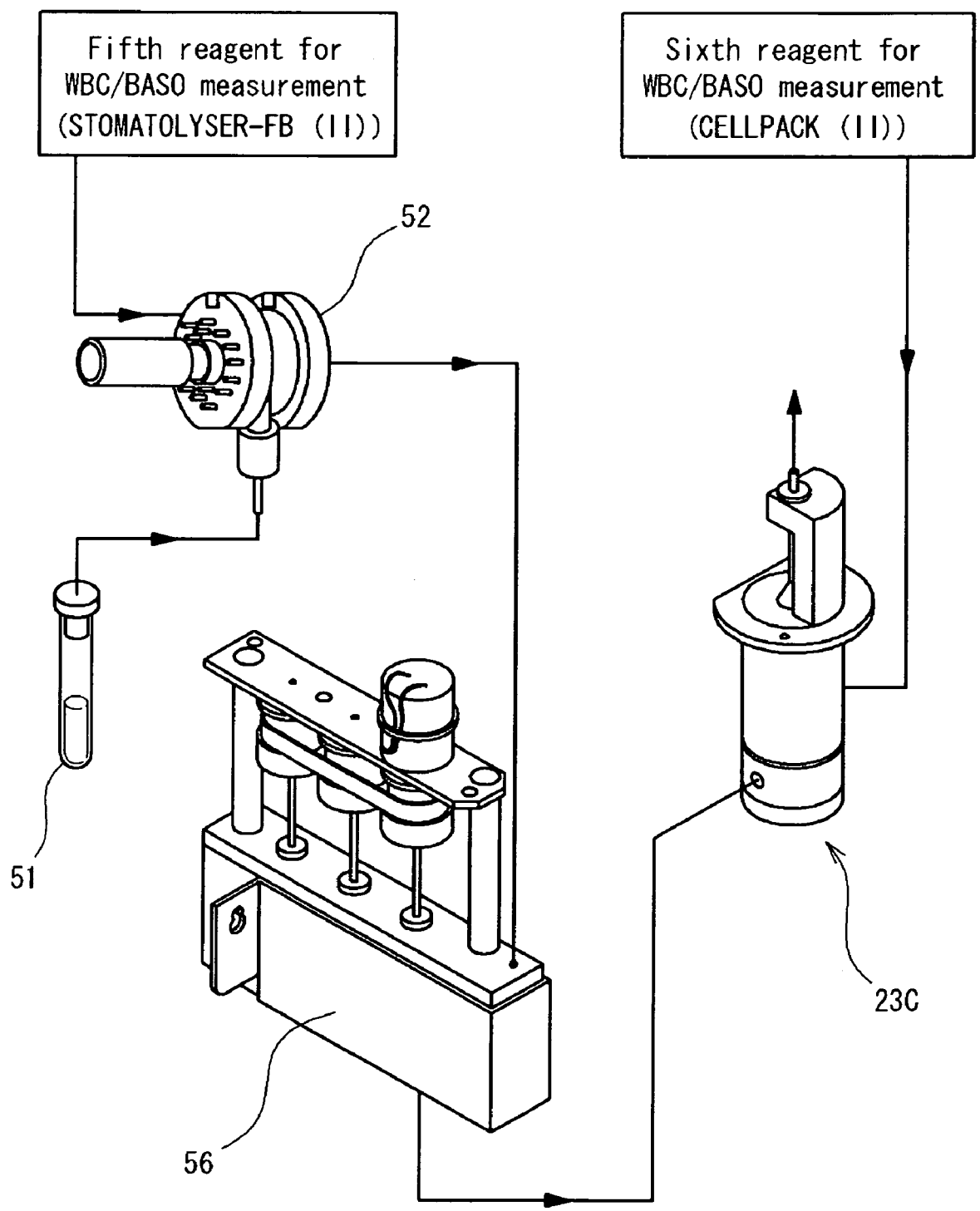
FIG. 6 illustrates the flow of a WBC/BASO measurement in the hemocytometer of FIG. 1.

The optical detector 23C carries out the fraction measurement of the number of white blood cells (WBC measurement), the fraction measurement of basophil in white blood cells (BASO measurement), and the fraction measurement of neutrophil (NEUT), lymph cells (LYMPH), monocytes (MONO), eosinophils (EO), and basophils (BASO) in white blood cells (DIFF measurement). FIG. 6 illustrates the flow of the WBC measurement and the BASO measurement by the optical detector 23C. The blood in the blood collection tube 51 is sucked via a suction pipette into the sampling valve 52 and is quantitated in a predetermined amount. The quantitated blood is diluted by the fifth reagent and the resultant diluted sample is sent to a reaction chamber 56. Then, the reaction is performed in this status for ten and several seconds, thereby hemolyzing the red blood cells in the diluted sample.

The optical detector 23C receives the diluted sample and the sixth reagent and subjects the diluted sample and the sixth reagent to the WBC measurement and the BASO measurement using semiconductor laser based on the flow cytometry technique.

Figure 7:
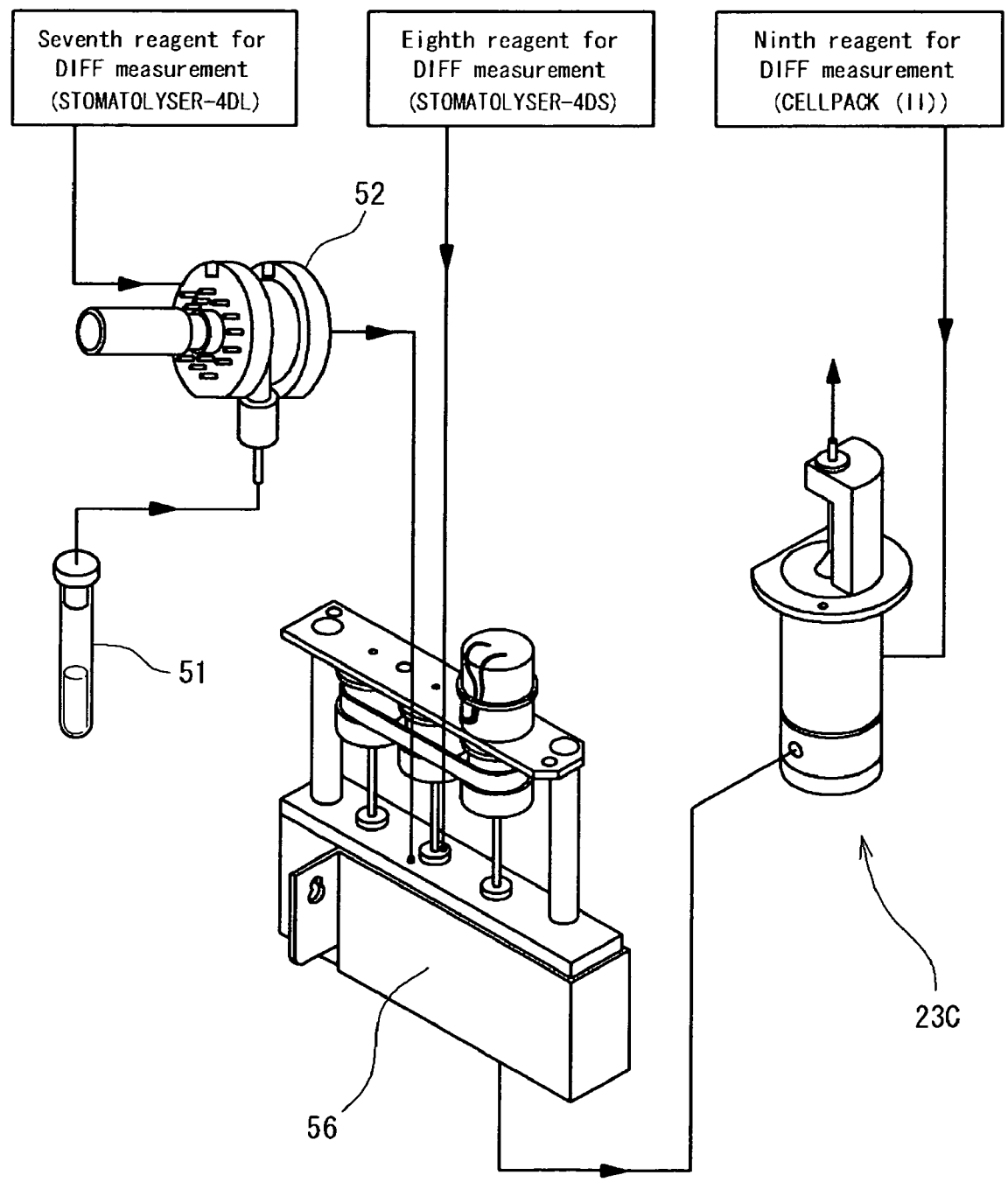
FIG. 7 illustrates the flow of a DIFF measurement in the hemocytometer of FIG. 1.

FIG. 7 illustrates the flow of the DIFF measurement by the optical detector 23C. The blood in the blood collection tube 51 is sucked via a suction pipette into the sampling valve 52 and is quantitated in a predetermined amount. The quantitated blood is diluted by the seventh reagent for the DIFF measurement and the resultant diluted sample is sent to the reaction chamber 56 while being simultaneously added with the eighth reagent for further dilution. Then, the reaction is performed in this status for several dozen seconds to hemolyze the red blood cells in the diluted sample, thereby staining white blood cell.

The optical detector 23C receives the diluted sample and the ninth reagent and subjects the diluted sample and the ninth reagent to the DIFF measurement using semiconductor laser based on the flow cytometry technique.

Figure 8:
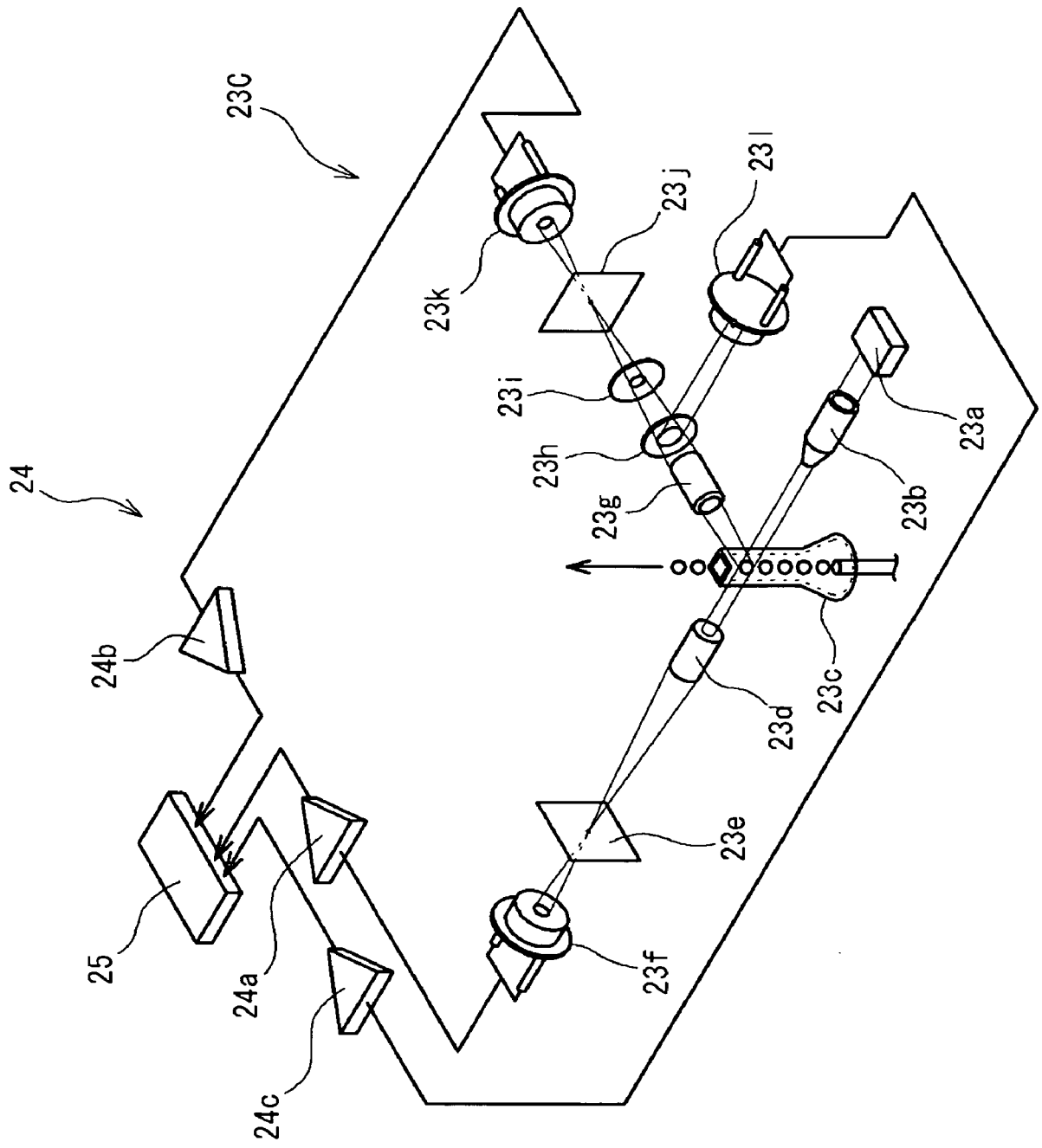
FIG. 8 illustrates the configuration of an optical detector in the hemocytometer of FIG. 1.

As shown in FIG. 8, the optical detector 23C includes: a light-emitting section 23a that emits laser light; an irradiation lens unit 23b; a sheath flow cell 23c to which laser light is irradiated; a light collection lens 23d provided on an extended line in a direction along which the laser light emitted from the light-emitting section 23a proceeds; a pinhole 23e and a PD (photodiode) 23f; a light collection lens 23g, a dichroic mirror 23h, an optical filter 23i, a pinhole 23j and a PD 23k which are provided in a direction intersecting with the direction along which the laser light emitted from the light-emitting section 23a proceeds; and an APD (avalanche photodiode) 23l provided at a side of the dichroic mirror 23h.

The light-emitting section 23a is provided to emit light to a sample flow including a measurement sample passing through the sheath flow cell 23c. The irradiation lens unit 23b is provided to convert the light emitted from the light-emitting section 23a to parallel light. The PD 23f is provided to receive forward-scattered light emitted from the sheath flow cell 23c.

The dichroic mirror 23h is provided to separate the side-scattered light and the side fluorescence emitted from the sheath flow cell 23c. Specifically, the dichroic mirror 23h is provided to cause the side-scattered light emitted from the sheath flow cell 23c to enter the PD 23k and to cause the side fluorescence emitted from the sheath flow cell 23c to enter the APD 23l. The PD 23k is provided to receive the side-scattered light. The APD 23l is provided to receive the side fluorescence. The PDs 23f, 23k and the APD 23l have a function to convert a received light signal to an electric signal, respectively.

The analog signal processing circuit 24 includes amplifiers 24a, 24b, and 24c. The amplifiers 24a, 24b, and 24c are provided to subject electric signals outputted from the PDs 23f, 23k and the APD 23l to amplification and waveform processings, respectively.

(Reagents Used in the Respective Measurements)

The measurements by the respective detectors 23A to 23C use various reagents such as diluent, sheath liquid, hemolytic agent, or stain solution (the first to ninth reagents). As these reagents, dedicated reagents (genuine products) guaranteed by the supplier of the hemocytometer 1 are recommended. The reason is therefor that the dedicated reagent is optimized for the hemocytometer 1 to include components for example so that an accurate analysis result can be obtained in the hemocytometer 1. The hemocytometer 1 according to this embodiment is designed through repeated evaluation experiments so that an accurate analysis result can be obtained through an analysis using the dedicated reagent. Thus, when any reagent (not-genuine product) other than the dedicated reagent for which the performance is guaranteed by the supplier of the hemocytometer 1 according to this embodiment is used to analyze a sample by the hemocytometer 1, an accurate analysis result is not guaranteed and the analysis result has a reduced reliability. The dedicated reagent may be any reagent guaranteed by the supplier regardless of whether the reagent can be used in apparatuses made by other companies.

In the hemocytometer 1 of this embodiment, the first reagent as a genuine product can be "CELLPACK (II)" (made by SYSMEX CORPORATION), the second reagent as a genuine product can be "SE sheath (II)" (made by SYSMEX CORPORATION), the third reagent as a genuine product can be "CELLPACK (II)" same as the first reagent, the fourth reagent as a genuine product can be "SULFOLYSER" (made by SYSMEX CORPORATION), the fifth reagent as a genuine product can be "STOMATOLYSER-FB(II)" (made by SYSMEX CORPORATION), the sixth reagent as a genuine product can be "CELLPACK (II)" same as the first and third reagents, the seventh reagent as a genuine product can be "STOMATOLYSER-4DL" (made by SYSMEX CORPORATION), the eighth reagent as a genuine product can be "STOMATOLYSER-4DS" (made by SYSMEX CORPORATION), and the ninth reagent as a genuine product can be "CELLPACK (II)".

A hard disk 31d of the data processing apparatus 3 (see FIG. 3) stores therein a database storing the correspondence between measurement items performed by the respective detectors 23A to 23C and the information regarding dedicated reagents used in the respective measurement items. FIG. 19 shows the relation between the measurement items and reagents in this database.

The memory 27 of the measurement section 2 (see FIG. 2) is configured to store information (determination result information) showing whether new reagent exchanged with the old one is dedicated reagent or not. Specifically, the memory 27 is configured to store the determination result information showing the determination result by the CPU 31a of the data processing apparatus 3 (which will be described later) with regard to whether new reagent exchanged with the old one is dedicated reagent or not, the details of which will be described later.

[Configuration of Data Processing Apparatus 3]

Figure 3:
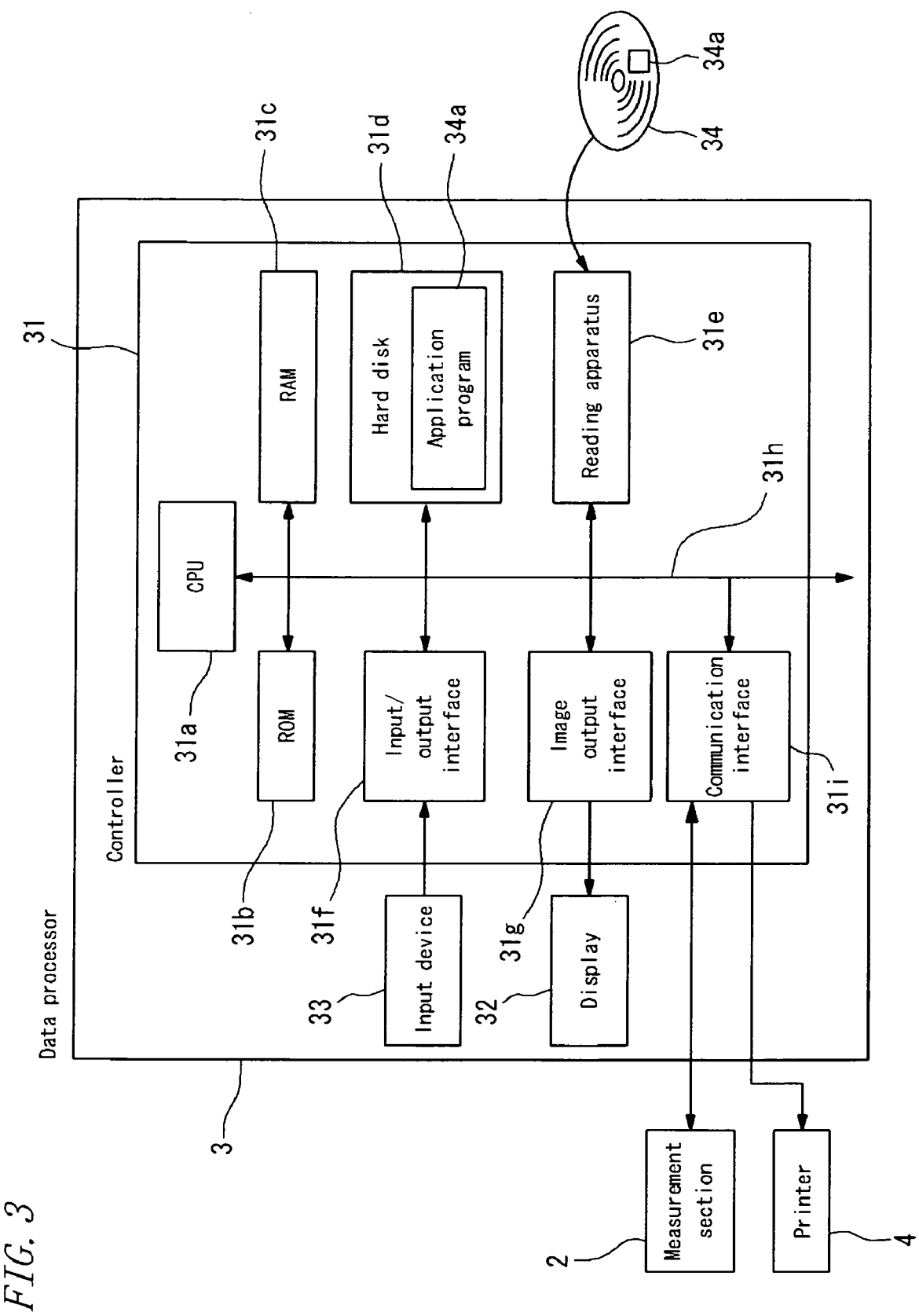
FIG. 3 is a block diagram illustrating the configuration of a data processing apparatus in the hemocytometer of FIG. 1.

As shown in FIG. 1, the data processing apparatus 3 is composed of a personal computer (PC) or the like. The data processing apparatus 3 includes: a controller 31; a display 32; and an input device 33. The data processing apparatus 3 has a function to accept an operation by a user to send an operation instruction to the measurement section 2 and receives measurement data (measurement value) from the measurement section 2 to process the measurement data to display the analysis result. As shown in FIG. 3, the controller 31 is composed of: a CPU 31a; a memorization section consisting of a ROM 31b, a RAM 31c, and a hard disk 31d; a reading apparatus 31e; an input/output interface 31f; an image output interface 31g; and a communication interface 31i. The CPU 31a, the ROM 31b, the RAM 31c, the hard disk 31d, the reading apparatus 31e, the input/output interface 31f, the image output interface 31g, and the communication interface 31i are connected by a bus 31h.

The CPU 31a is provided to execute a computer program memorized in the ROM 31b and a computer program loaded to the RAM 31c. The ROM 31b is configured by a mask ROM, PROM, EPROM, EEPROM or the like in which the computer program executed by the CPU 31a and the data used for this or the like are recorded.

The RAM 31c is configured by a SRAM or DRAM or the like. The RAM 31c is used to read a computer program recorded in the ROM 31b and the hard disk 31d. The RAM 31c is also used as an operation region of the CPU 31a when these computer programs are executed.

In the hard disk 31d, there are installed various computer programs to be executed by the CPU 31a and data used to execute the computer programs, such as an operating system and an application program. An application program 34a for allowing the data processing apparatus 3 to realize a predetermined function (e.g., a reagent determination function, a screen display function, a print function as will be described later) is also installed in this hard disk 31d.

The reading apparatus 31e is configured by a flexible disk drive, a CD-ROM drive, a DVD-ROM drive or the like. The reading apparatus 31e can read a computer program or data recorded in a mobile recording medium 34. The mobile recording medium 34 stores therein the application program 34a. The computer as a data processing apparatus 3 can read the application program 34a from the mobile recording medium 34 to install the application program 34a in the hard disk 31d.

It is noted that the application program 34a can be provided not only from the mobile recording medium 34 but also from an external device connected to the computer to have communication therebetween via an electric communication line (which may be wired or wireless). For example, the application program 34a can be also stored in a hard disk of a server computer on the Internet and the computer may access this server computer to download the application program 34a to install the application program 34a in the hard disk 31d.

In the hard disk 31d, an operating system providing a graphical user interface environment such as Windows manufactured and sold by Microsoft Corporation is installed for example. The following description will assume that the application program 34a in this embodiment operates on the above-mentioned operating system.

The input/output interface 31f is configured, for example, by a serial interface such as a USB, IEEE1394 or RS-232C, a parallel interface such as an SCSI, IDE or IEEE1284, and an analog interface composed of a D/A converter, an A/D converter or the like. The input/output interface 31f is connected to the input device 33 composed of a keyboard and a mouse. A user can use the input device 33 to input data to the data processing apparatus 3.

The communication interface 31i is an Ethernet interface for example. The data processing apparatus 3 can use the communication interface 31i to use a predetermined communication protocol (TCP/IP) to send data to and to receive data from the measurement section 2 connected by LAN cable. A printer 4 is connected to the data processing apparatus 3 via the communication interface 31i.

An image output interface 31g is connected to the display 32 composed of LCD, CRT or the like. The image output interface 31g is designed to receive a video signal from the CPU 31a to output the video signal to the display 32. Based on the inputted video signal, the display 32 displays an image (screen).

Figure 21:
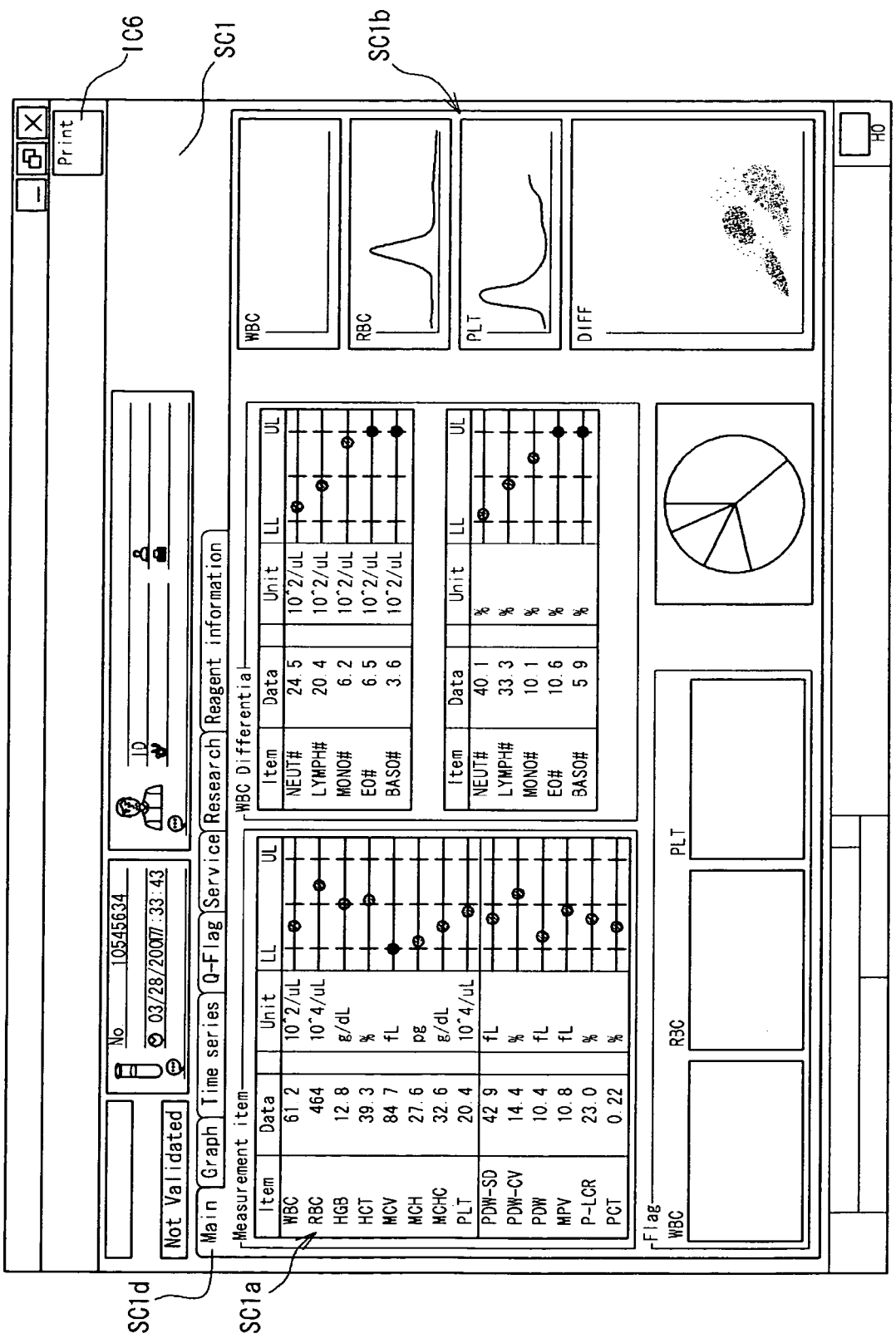
FIG. 21 illustrates an example of an analysis result display screen displayed in the data processing apparatus of the hemocytometer of FIG. 1 when genuine reagent is used.

In this embodiment, the CPU 31a has a function to process the measurement value measured by the measurement section 2 to obtain an analysis result to output to the image output interface 31g a video signal depending on an analysis result display screen for displaying the analysis result. FIG. 21 illustrates an example of an analysis result display screen SC1 displayed in the display 32 of the data processing apparatus 3. The analysis result display screen SC1 includes: a display region SC1a for displaying the numerical data regarding the respective measurement items; and a display region SC1b for displaying a scattergram or a particle size distribution diagram (hereinafter referred to as "scattergram or the like") showing the distribution of the number or size of particles in a predetermined item (e.g., WBC, RBC, PLT, DIFF).

Figure 9:
FIG. 9 illustrates a reagent exchange screen displayed in the data processing apparatus in the hemocytometer of FIG. 1.
Figure 10:
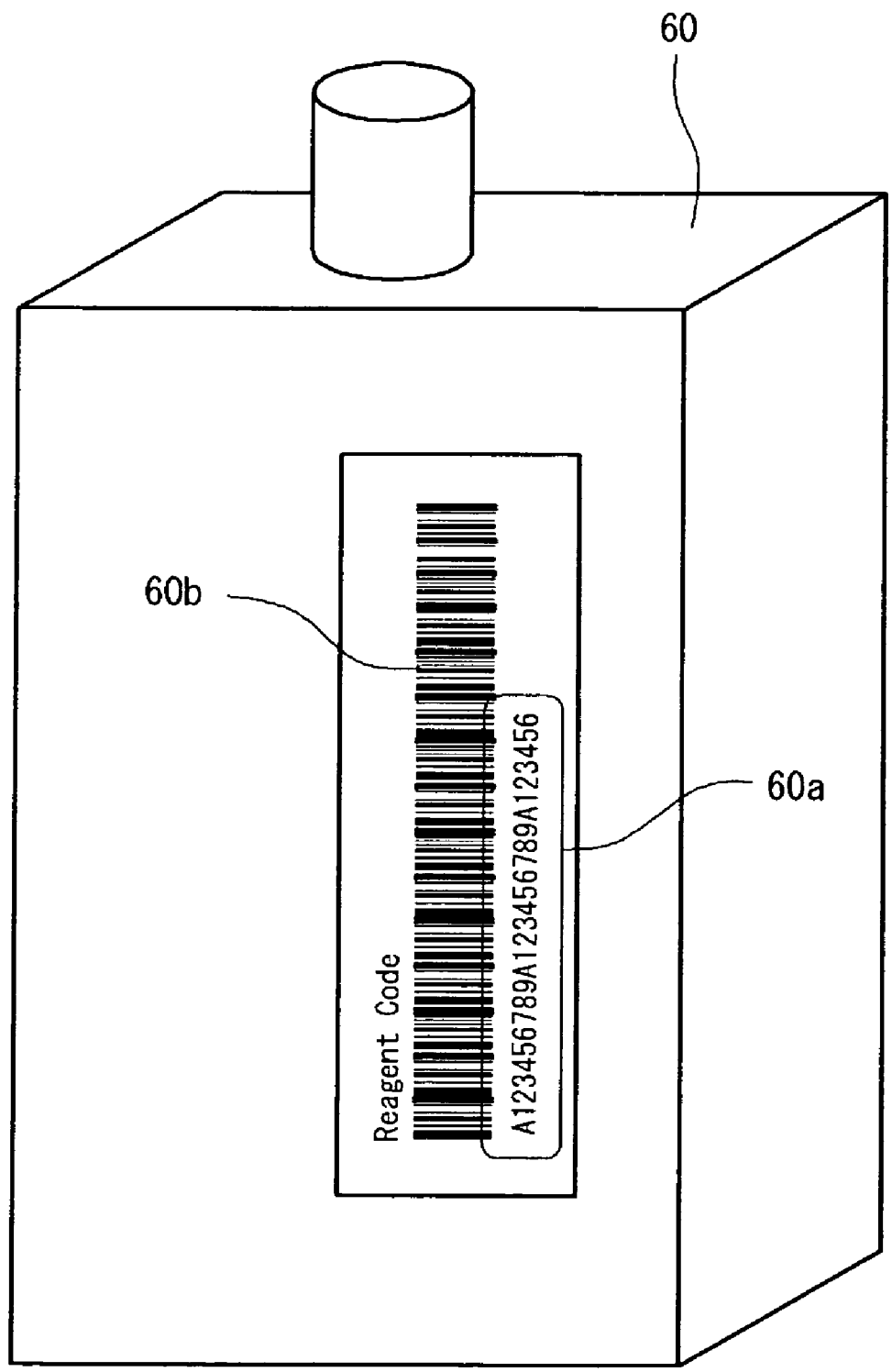
FIG. 10 is a perspective view illustrating a reagent container used in the hemocytometer of FIG. 1.

In this embodiment, when the reagent used by the user in the measurement section 2 is exchanged with the new one, the CPU 31a outputs a video signal to the image output interface 31g so that a reagent exchange screen SC3 shown in FIG. 9 is displayed in the display 32. This reagent exchange screen SC3 is configured to allow the user to input a unique Reagent Code 60a consisting of 27 digits provided to a reagent container 60 (see FIG. 10). The hemocytometer 1 is also configured to allow the user to input the Reagent Code 60a by using a bar code reading apparatus (not shown) to read a bar code 60b displayed at the upper part of the Reagent Code 60a. The Reagent Code means information unique to the dedicated reagent (genuine product) that is appropriate for the measurement by the measurement section 2 (e.g., an encrypted reagent code of 27 digits storing an expiration date or a lot No. for providing traceability for example). The Reagent Code 60a is encrypted by a predetermined function and is configured so that the CPU 31a can determine, based on encrypted alphameric characters, whether or not the reagent is a dedicated reagent (genuine product) appropriate for the use by the measurement section 2.

The CPU 31a is also configured to measure the remaining amount of the reagent being used to store the information for the remaining amount and the Reagent Code 60a of the reagent in a storage section such as the hard disk 31d or a RAM 31c for example. The storage section can store the Reagent Codes and the information for remaining amounts of a plurality of reagents used in the past as a reagent exchange hostory. The CPU 31a is configured to determine, based on both of the Reagent Code 60a and the information for the remaining amount, whether or not the new reagent exchanged with the old one is dedicated reagent (genuine product).

[Procedure for Determining Dedicated Reagent]

Figure 11:
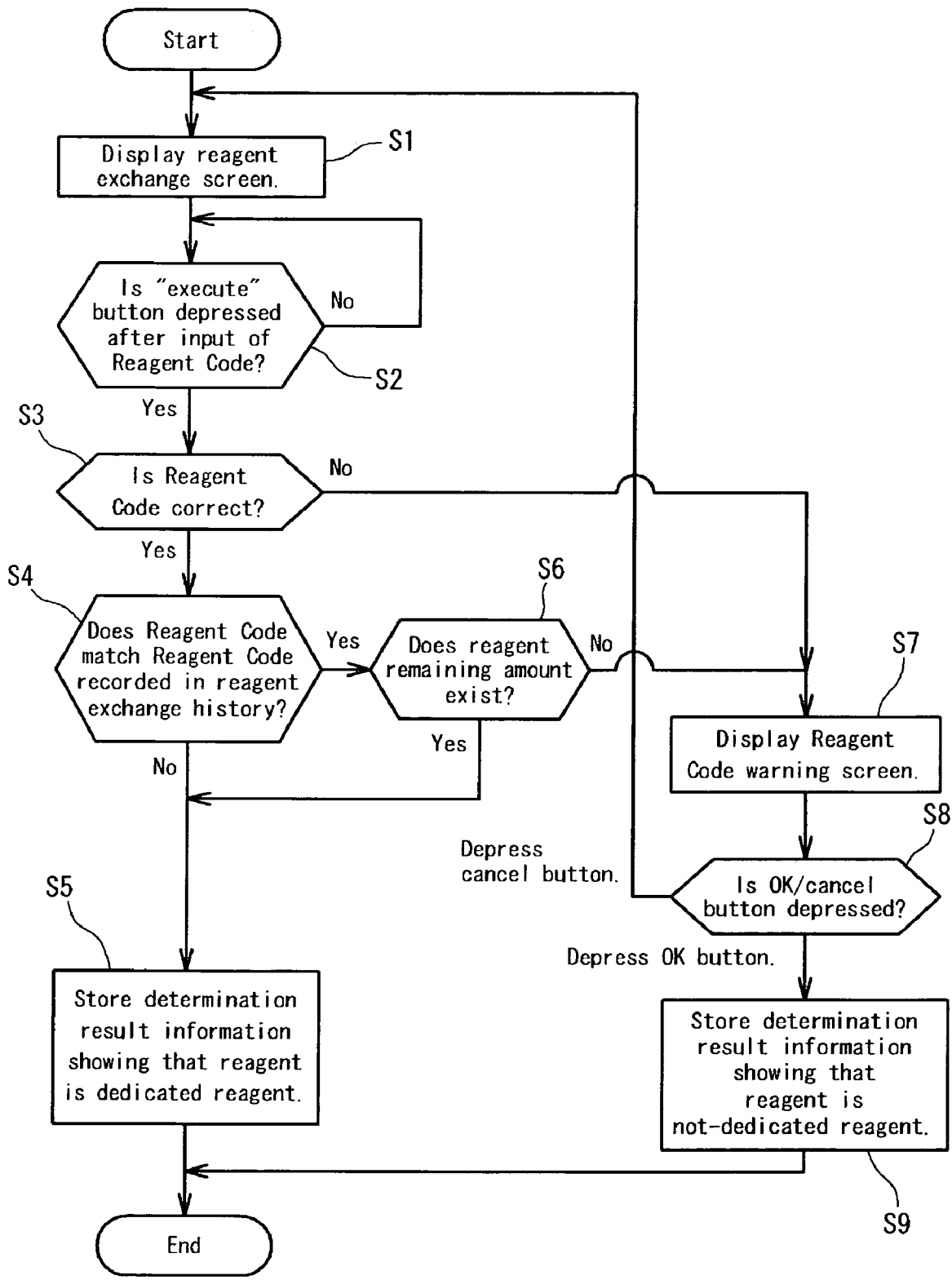
FIG. 11 is a flowchart illustrating a control for determining in the hemocytometer of FIG. 1 whether new reagent offered in exchange for the old one is dedicated reagent (genuine product) or not.
Figure 12:
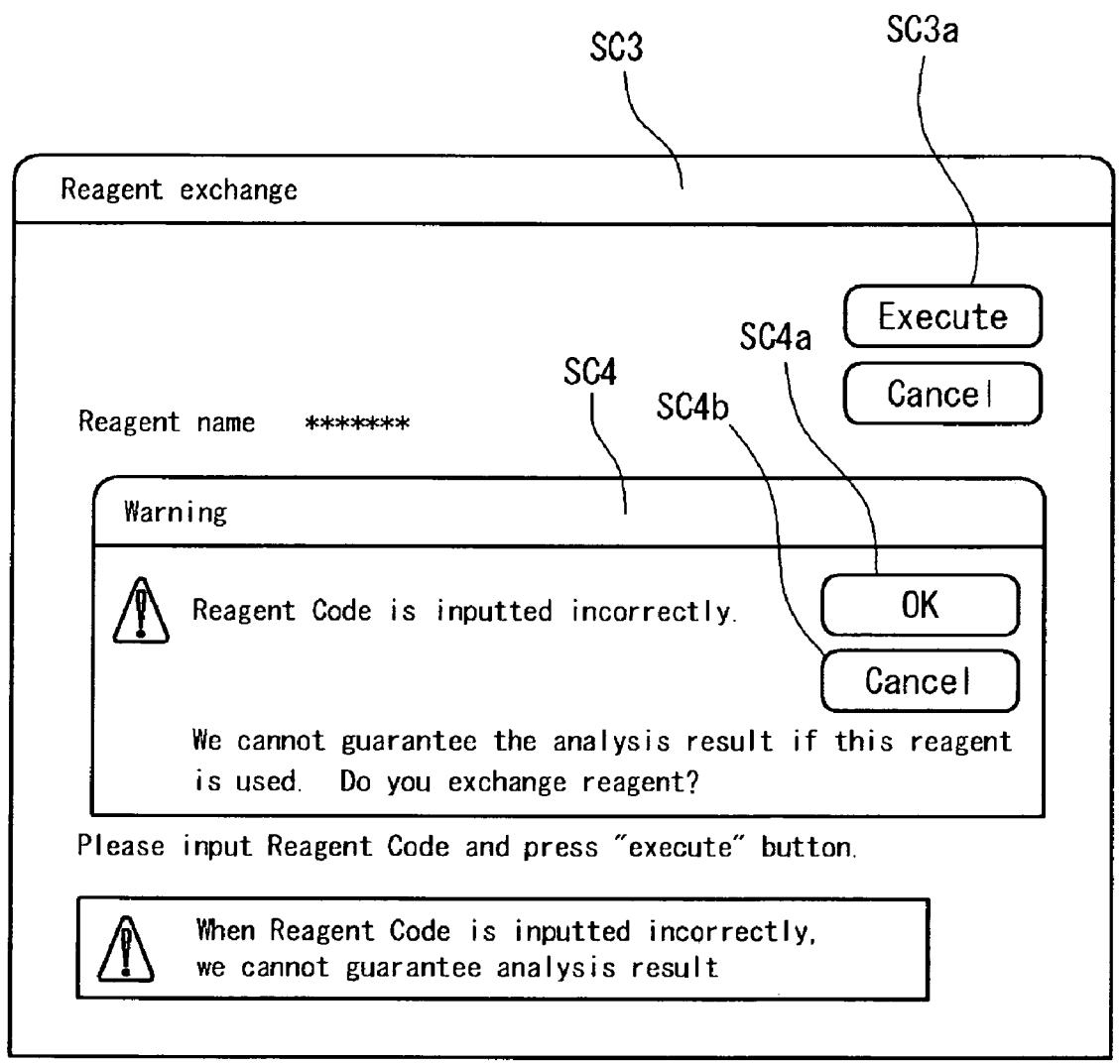
FIG. 12 illustrates a Reagent Code warning screen displayed in the data processing apparatus of the hemocytometer of FIG. 1.

FIG. 11 is a flowchart illustrating the operation for determining in the hemocytometer 1 of this embodiment whether or not the new reagent offered in exchange for the old one is dedicated reagent (genuine product). FIG. 12 illustrates a Reagent Code warning screen in the hemocytometer 1 of this embodiment shown in FIG. 1. Next, with reference to FIG. 9 to FIG. 12, a genuine product determination operation will be described that determines, in the hemocytometer 1 of this embodiment, whether or not the new reagent offered in exchange for the old one is dedicated reagent (genuine product). The operation described below is an operation controlled by the CPU 31a of the data processing apparatus 3.

In Step S1 of FIG. 11, the reagent exchange screen SC3 shown in FIG. 9 is displayed to prompt the user to input a Reagent Code. The reagent exchange screen SC3 is displayed on the display 32 when a reagent exchange icon in a menu screen (not shown) is double-clicked by the user. Step S2 allows the user to input, through the reagent exchange screen SC3, the Reagent Code 60a of 27 digits (see FIG. 10) applied to the reagent to determine whether an "execute" button SC3a is depressed (selected) or not. When the "execute" button SC3a is not depressed, then this determination is repeated. When the "execute" button SC3a is depressed, Step S3 determines whether the inputted Reagent Code is correct or not. Specifically, Step S3 determines whether the inputted Reagent Code is composed of alphameric characters correctly prepared based on an algorithm used in the encryption. When the inputted Reagent Code is the correct one, then the lot No. and the expiration date stored in the alphameric characters in an encrypted manner are decrypted and are displayed in the respective sections in the reagent exchange screen SC3. When the inputted Reagent Code is the correct one, then the processing proceeds to Step S4.

When the Reagent Code is not the correct one, then Step S7 displays a Reagent Code warning screen SC4 as shown in FIG. 12. The Reagent Code warning screen SC4 displays a warning message that the Reagent Code is not correctly inputted and the analysis result cannot be guaranteed and the user is asked to determine whether the reagent exchange is performed or not.

Step S8 of FIG. 11 determines whether an OK button SC4a or a cancel button SC4b in the Reagent Code warning screen SC4 is depressed. When the cancel button SC4b is depressed, then the processing returns to Step S1. When the OK button SC4a is depressed, Step S9 stores, in a storage section such as the RAM 31c, the determination result information showing that the reagent is nondedicated reagent (not-genuine product), thereby completing the operation.

When the Reagent Code is the correct one, Step S4 determines whether or not the inputted Reagent Code is identical with the one of Reagent Codes of a plurality of reagents used in the past stored in the storage section as a part of a reagent exchange history. When the identical one is not found, then the processing goes to Step S5 to store, in the storage section, the determination result information showing that the reagent is dedicated reagent (genuine product), thereby completing the operation.

When the inputted Reagent Code is identical with any one of a plurality of reagents stored in the storage section, Step S6 checks the information regarding the remaining amount of the reagent that is stored in the storage section together with the Reagent Code. When the storage section stores no reagent remaining amount corresponding to the inputted Reagent Code, this means that all reagents are already used and are exchanged with the new ones. Thus, it can be determined that a nondedicated reagent is falsely used as a dedicated reagent (e.g., another reagent (not-genuine product) may be refilled in a container of the reagent to be exchanged, or a Reagent Code applied to dedicated reagent (genuine product) used in the past may be inputted and the reagent exchanged as the new one may be a not-genuine product). Thus, when there is no reagent remaining amount stored in the storage section in Step S6, then the processing proceeds to Step S7 to display the Reagent Code warning screen SC4. When there is a reagent remaining amount, the reagent is determined as dedicated reagent (genuine product) and the processing proceeds to Step S5. By carrying out the genuine product determination operation when the reagent is exchanged with the new one as described above, there can be supressed where any reagent unchecked with regard to whether the new reagent is a dedicated reagent (genuine product) or not is newly set as a substitute for the old one and is used for measurement and analysis.

[Procedure for Updating Reagent Information]

Figure 13:
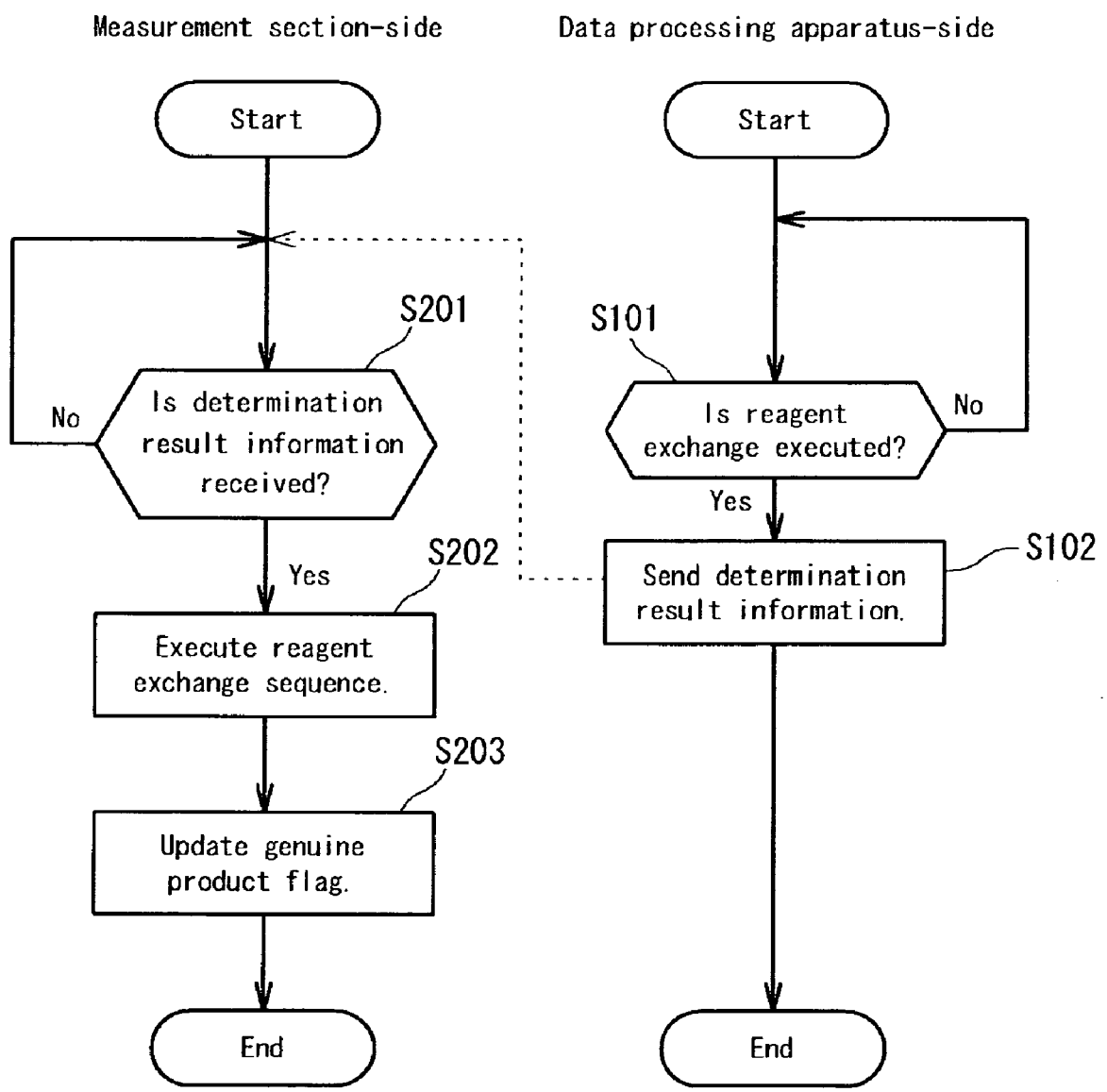
FIG. 13 is a flowchart illustrating a control in the hemocytometer of FIG. 1 for updating information showing whether the reagent is a genuine product or not.

FIG. 13 is a flowchart illustrating the operation for updating the information showing whether the reagent is a genuine product or not in the hemocytometer 1 according to this embodiment. Next, with reference to FIG. 11 and FIG. 13, an operation for updating a genuine product flag in the hemocytometer 1 according to this embodiment will be described. This operation for updating a genuine product flag updates the information showing whether the reagent is a genuine product or not. The operation described below is an operation controlled by the CPU 31a of the controller 31 of the data processing apparatus 3 and the CPU 28 of the measurement section 2.

First, the data processing apparatus 3 in Step S101 of FIG. 13 determines whether the reagent exchange is performed or not. When the reagent exchange is not performed, then this determination is repeated. Specifically, whether the reagent exchange is performed or not is determined based on whether the genuine product determination operation in the flow shown in FIG. 11 is completed or not. When the genuine product determination operation in the flow shown in FIG. 11 is completed, this means that the reagent exchange is performed. Thus, Step S102 transmits a signal showing the determination result information to the measurement section 2, thereby completing the operation.

In Step S201, the measurement section 2 receives the signal showing the determination result information that is transmitted from the data processing apparatus 3. In Step S202, a sequence control in the reagent exchange is performed. This sequence control in the reagent exchange is a preparative operation for performing the next measurement. This sequence control will be described specifically. After the reagent exchange, air may exist in a tube through which the reagent flows or no reagent may exist in a space in a tube that should accommodate the reagent. To solve this, the sequence control in the reagent exchange sucks reagent from a newly-set reagent container and fills reagent in the tube.

Next, based on the received signal showing the determination result information, Step S203 stores, in the memory 27 (see FIG. 2), the information showing whether the reagent is dedicated reagent (genuine product) or not. Specifically, when the reagent is dedicated reagent (genuine product), then the information showing whether the reagent is dedicated reagent (genuine product) or not is updated so that a genuine product flag stored in the memory 27 is in an ON status. When the reagent is nondedicated reagent (not-genuine product), then the information showing whether the reagent is dedicated reagent (genuine product) or not is updated so that a genuine product flag stored in the memory 27 is in an OFF status. Thereafter, the operation of the measurement section 2 is completed.

[Operation Procedure for Starting Hemocytometer Up]

Figure 14:
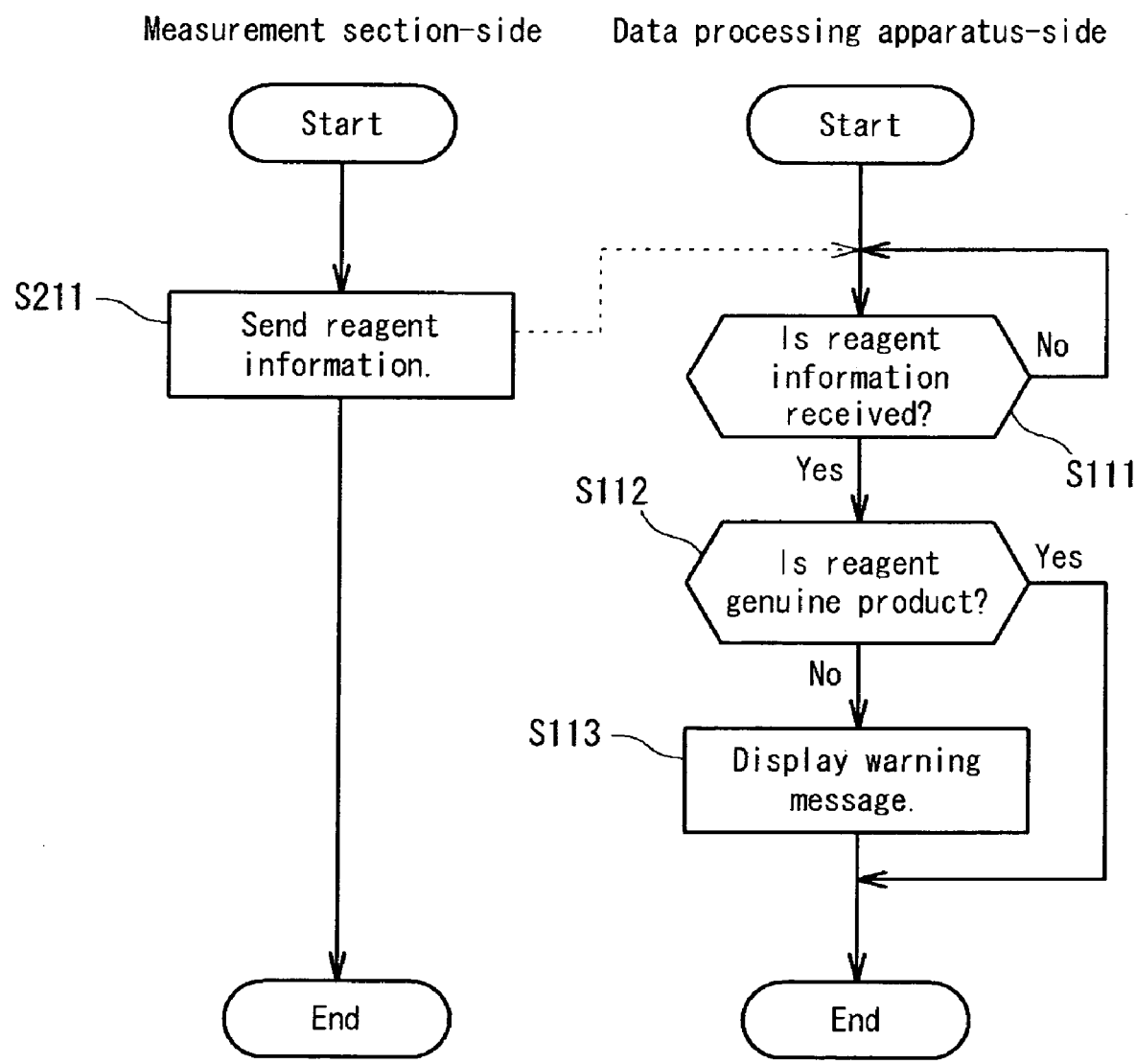
FIG. 14 is a flowchart illustrating a control in the hemocytometer of FIG. 1 for a startup operation.
Figure 15:
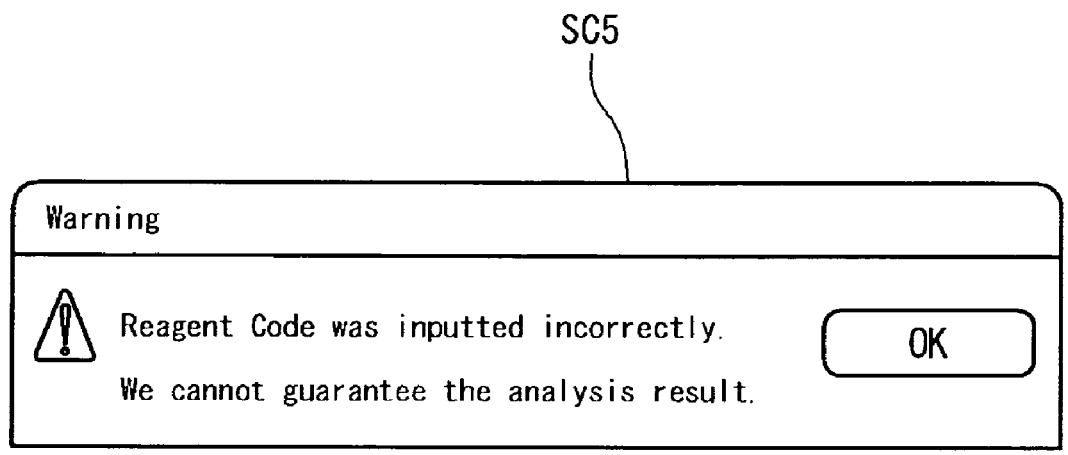
FIG. 15 illustrates the warning screen displayed in the data processing apparatus of the hemocytometer of FIG. 1.

FIG. 14 is a flowchart illustrating the operation at the startup of the hemocytometer 1 in this embodiment. FIG. 15 illustrates a warning screen of the hemocytometer 1 shown in FIG. 1. Next, with reference to FIG. 14 and FIG. 15, the operation at the startup of the hemocytometer 1 in this embodiment will be described. The operation described below is an operation controlled by the CPU 31a of the controller 31 of the data processing apparatus 3 and the CPU 28 of the measurement section 2.

First, Step S211 of FIG. 14 sends a reagent information signal to the data processing apparatus 3 based on the status of the genuine product flag stored in the memory 27 of the measurement section 2. Specifically, when the genuine product flag is in the ON status, a signal showing that the to-be-used reagent is dedicated reagent (genuine product) is sent to the data processing apparatus 3. When the genuine product flag is in the OFF status, a signal showing that the to-be-used reagent is nondedicated reagent (not-genuine product) is sent, thereby completing the operation.

In Step S111, the data processing apparatus 3 receives the reagent information signal sent from the measurement section 2. In Step S112, whether the reagent is dedicated reagent (genuine product) or not is checked based on the received reagent information signal. When the reagent is dedicated reagent (genuine product), then the operation is completed. When the reagent is nondedicated reagent (not-genuine product) on the other hand, Step S113 displays a warning screen SC5 as shown in FIG. 15. The warning screen SC5 displays a warning message that a Reagent Code is not correctly inputted during the reagent exchange and the analysis result cannot be guaranteed. By displaying the warning screen SC5 at the startup as described above, the user can recognize, prior to the start of measurement and analysis, that the to-be-obtained analysis result has a low reliability. Thereafter, the operation of the data processing apparatus 3 is completed.

[Procedure for Measurement and Analysis Operations of Hemocytometer]

Figure 16:
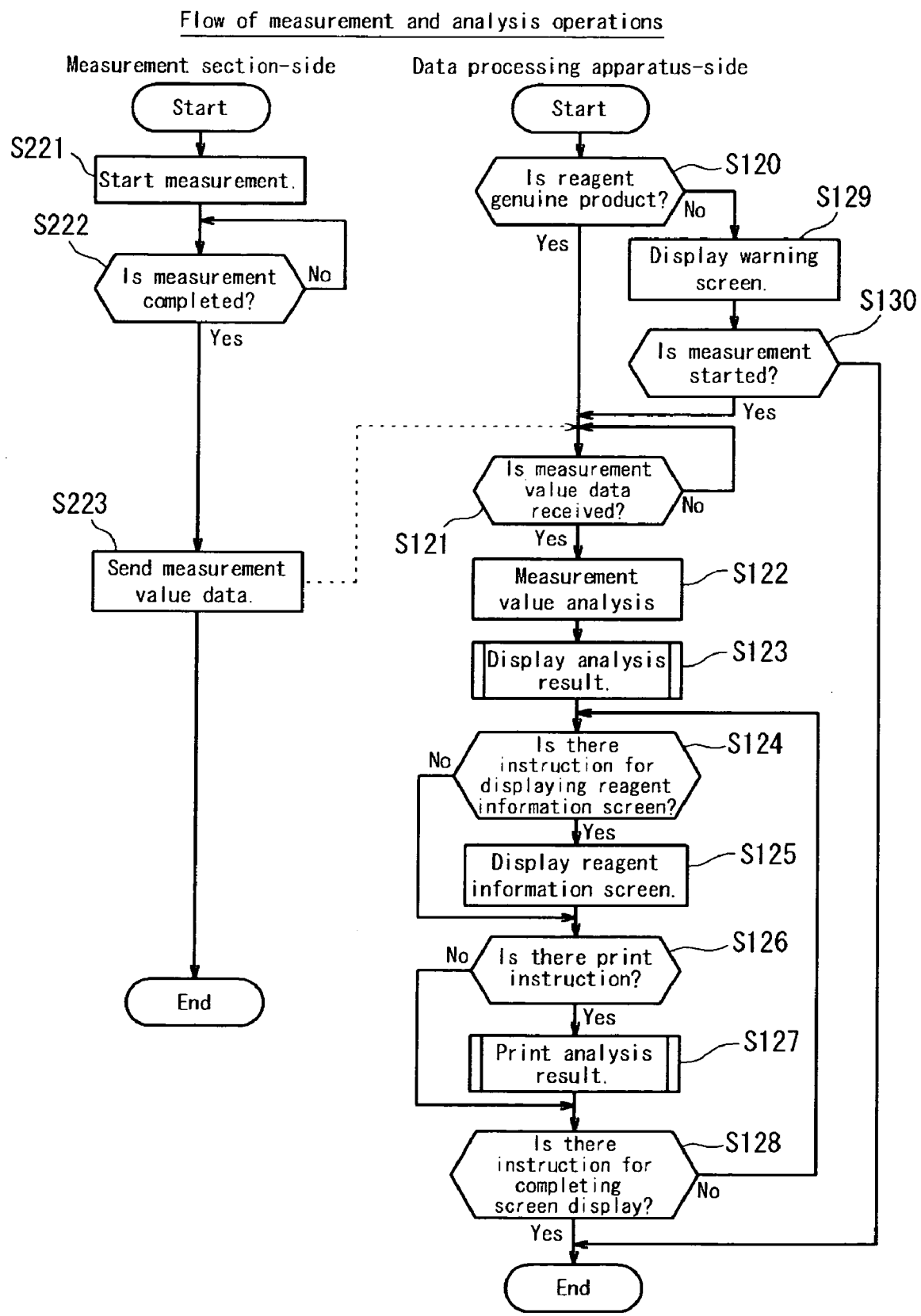
FIG. 16 is a flowchart illustrating a control in the hemocytometer of FIG. 1 of measurement and analysis operations.

FIG. 16 is a flowchart illustrating the measurement and analysis operations in the hemocytometer 1 according to this embodiment. Next, the following section will describe the measurement and analysis operations by the hemocytometer 1 of this embodiment including the display of an analysis result by the display 32 and an operation by the printer 4 to print the analysis result.

First, when the start of a measurement operation is instructed, then the data processing apparatus 3 in Step S120 determines whether the reagent to be used in the analysis is a genuine product or not. When the reagent is a genuine product, then the processing proceeds to Step S121. When the reagent is not a genuine product, then Step S129 shows that the reagent is not a genuine product and displays a warning screen in the display 32 through which the user is allowed to select the start of a measurement or the cancel of a measurement. Then, the processing proceeds to Step S130. When the start of a measurement is selected through the warning screen in Step S130, then the processing proceeds to Step S121. When the cancel of a measurement is selected, then the measurement is cancelled, thereby completing the processing (Step S130). By doing this, a situation can be prevented where the user mistakenly uses a not-genuine reagent for measurement while not knowing that the reagent is not a genuine product and not wanting to perform the measurement by the not-genuine product.

On the other hand, the measurement section 2 in Step S221 starts a blood measurement by the measurement section 2. Step S222 determines whether the measurement is completed or not. When the measurement is not completed, this determination is repeated while continuing the measurement. When the measurement is completed, then Step S223 sends the measurement value data via the LAN adapter 29 (see FIG. 2) to the data processing apparatus 3, thereby completing the operation of the measurement section 2.

In Step S121, the data processing apparatus 3 determines whether the measurement value data sent from the measurement section 2 is received or not. When the measurement value data is received, the measurement value is subjected to a processing (analysis processing) in Step S122 based on the received measurement value data. Then, Step S123 performs an operation to display the analysis result in the display section 32.

(Processing Procedure for Displaying Analysis Result)

Figure 17:
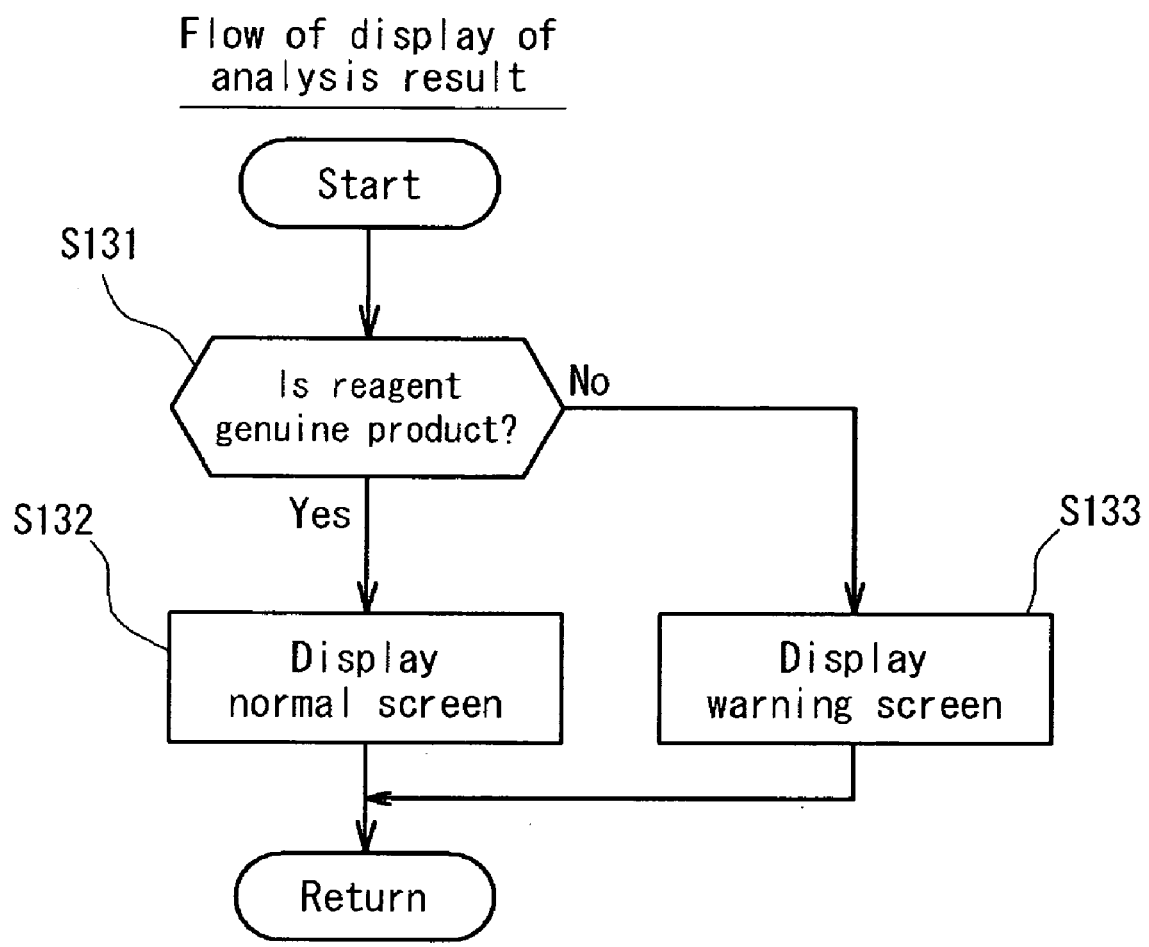
FIG. 17 is a flowchart illustrating an analysis result display control in the hemocytometer of FIG. 1.

FIG. 17 is a flowchart illustrating an analysis result display control of the hemocytometer 1 according to this embodiment. In Step S131, the data processing apparatus 3 determines whether the reagent used in the analysis is a genuine product or not. This determination is performed based on the check result checked in the operation at the startup in Step S112 shown in FIG. 14.

When the reagent used in the analysis is a genuine product, then the processing proceeds to Step S132 to display the normal analysis result display screen SC1 shown in FIG. 21 in the display 32. The analysis result display screen SC1 is a display in which a main tab SC1d is selected. The display region SC1a displays numerical data and the display region SC1b displays a scattergram or the like.

Figure 22:
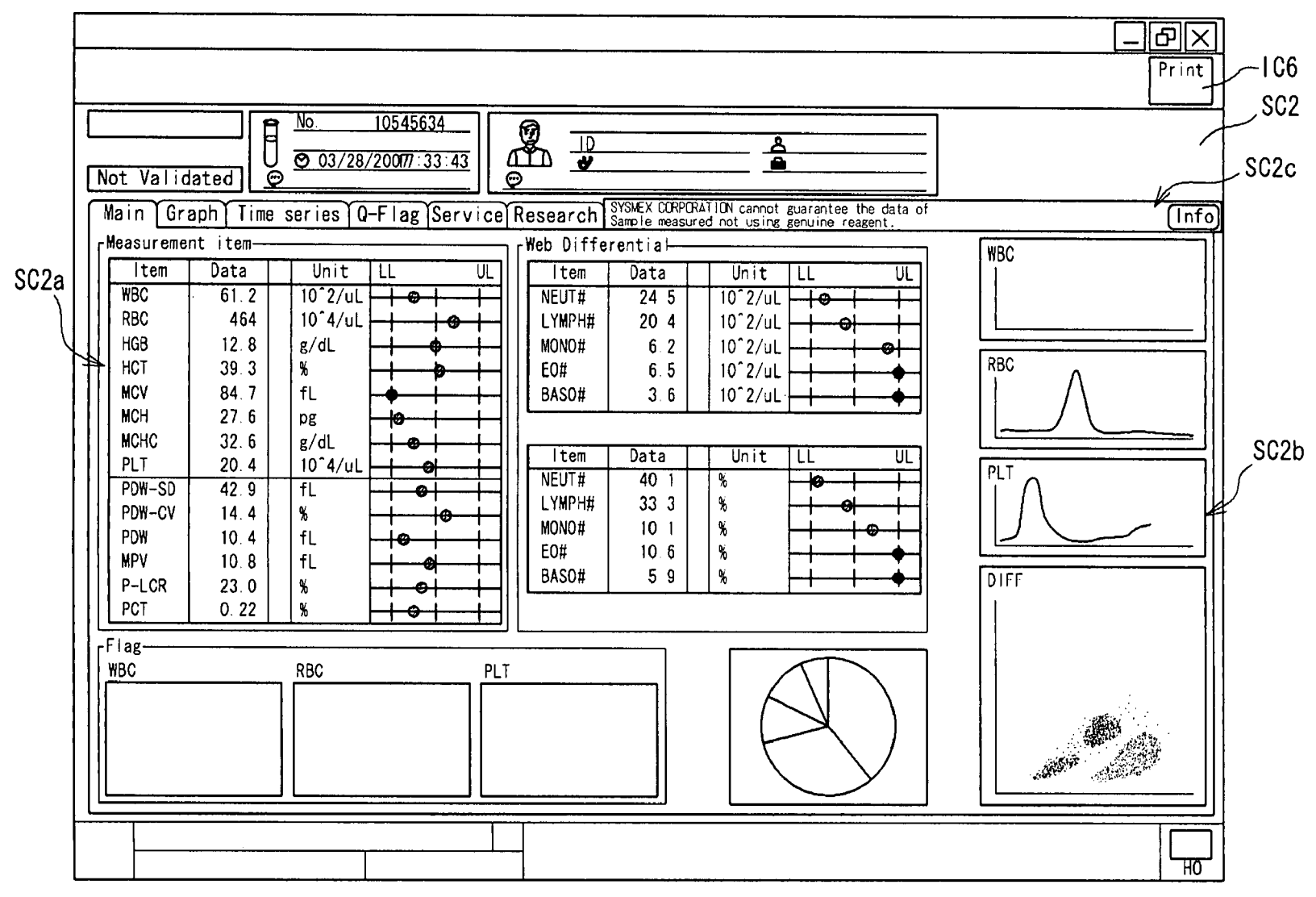

When the reagent used in the analysis is a not-genuine product, then the processing proceeds to Step S133 to display, in the display 32, an analysis result display screen SC2 including a warning message as shown in FIG. 22. This analysis result display screen SC2 is obtained by adding a note SC2c to the normal analysis result display screen SC1 of FIG. 21. This note SC2c shows a text display of information (reliability information) that the reagent used in the analysis is a not-genuine product and the supplier of the hemocytometer 1 cannot guarantee the analysis result. Thus, the user can securely recognize, upon seeing the reliability information of this note SC2c together with the analysis result, that the analysis result has a low reliability.

The analysis result display screen SC2 in FIG. 22 on the other hand cannot allow the user to identify which measurement item leads to an analysis result having a low reliability. To solve this, the reliability information as shown in FIG. 23 to FIG. 25 can be also displayed as a modification example.

FIG. 23 shows an example in which reliability information is added to the respective measurement items in a numerical data display region SC2a. Specifically, warning marks (icons) IC1a to IC1f as a reminder regarding reliability information are added so as to correspond to the measurement item names and numerical data. The warning marks IC1a to IC1f can be added to be followed by the text showing the measurement item names and numerical data (IC1a, IC1d) or to follow such text (IC1b, IC1e) or also can be added to the background (IC1c, IC1f). Through any of these patterns, the user can accurately recognize, upon seeing the numerical data display region SC2a, which measurement item leads to an analysis result having a low reliability.

Figure 24:
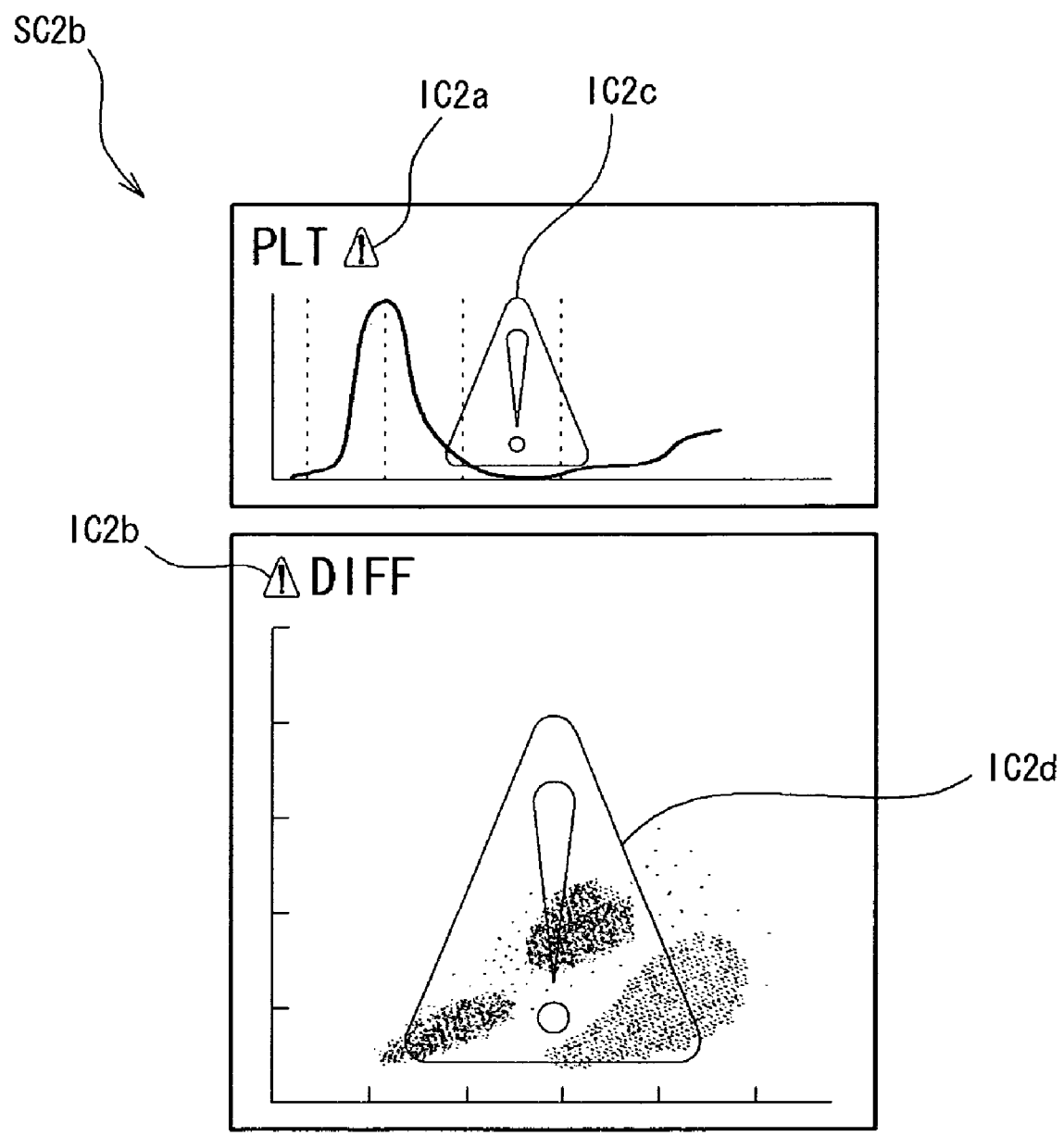
FIG. 24 illustrates a modification example of the analysis result display screen displayed in the data processing apparatus of the hemocytometer of FIG. 1 when not-genuine reagent is used.

FIG. 24 shows an example in which reliability information is added to a display region SC2b for displaying a scattergram for example. This example also uses warning marks IC2a to IC2d as a reminder regarding the reliability information. A warning mark can be added to be followed by text showing a item name of a scattergram for example (IC2b) or to follow such a text (IC2a) or can be also added to the background. Alternatively, a warning mark can be also added to the background of a scattergram for example (IC2c, IC2d).

FIG. 25 shows an example in which reliability information is added to the numerical data display region SC2a as in the example shown in FIG. 23. FIG. 25 is different from FIG. 23 in that the reliability information includes reagent information. Specifically, icons IC3a to IC3c obtained by putting "×" marks on different reagent container marks for the respective reagents are used as warning marks showing reliability information. The warning marks correspond to the text showing measurement item names. In the example of FIG. 25, the user can recognize not only which measurement item leads to an analysis result having a low reliability but also which reagent among a plurality of reagents used for the measurement having a low reliability is a not-genuine product. The icons IC3a to IC3c may be also put on text showing numerical data.

Figure 18:
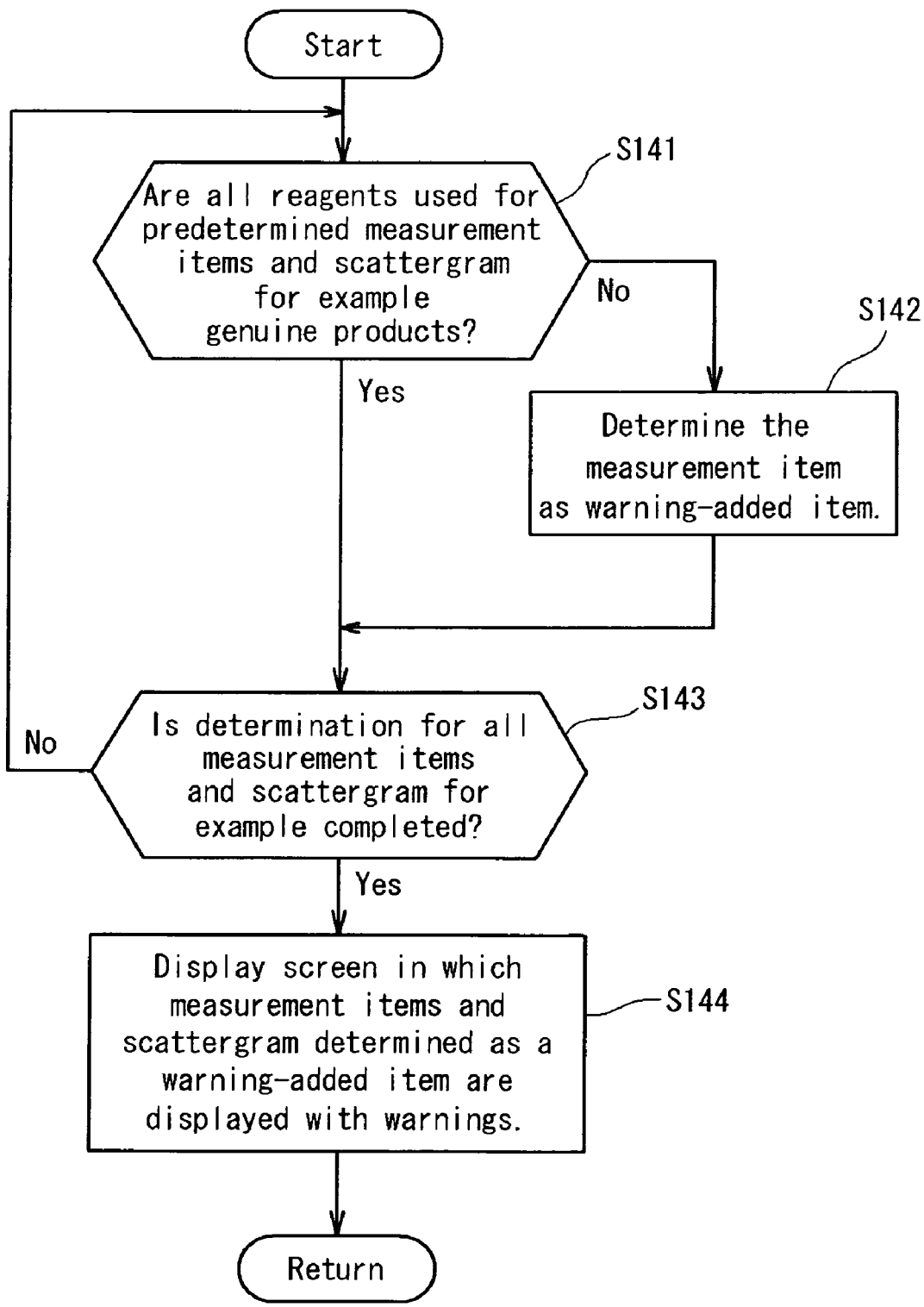
FIG. 18 is a flowchart illustrating a warning screen display control of the hemocytometer of FIG. 1.

When the reliability information is put on the numerical data or scattergram for example of the respective measurement items as described above, Step S133 in FIG. 17 performs a control as described below. FIG. 18 is a flowchart illustrating the control of a screen display including a warning message. The data processing apparatus 3 in Step S141 determines whether the reagent used in the respective measurement items and scattergram for example is a genuine product or not. When the reagent used in the respective measurement items and scattergram for example is a genuine product, Step S143 determines whether the determination is completed with regard to all measurement items and scattergram for example. When the determination is not yet completed, then the processing returns to Step S141. When the reagent used in the predetermined measurement items and scattergram for example is not a genuine product, Step S142 determines that warning marks (reliability information) are added to the measurement items and scattergram for example and the processing proceeds to Step S143.

When Step S143 determines that the determination for all measurement items and scattergram for example is completed, then Step S144 allows the display 32 to display the analysis result display screen SC2 (SC2a and SC2b of FIG. 23 to FIG. 25) in which warning marks are put on the measurement items and scattergram for example determined to have thereon warning marks. Thereafter, the processing proceeds to Step S124 of FIG. 16.

Figure 26:
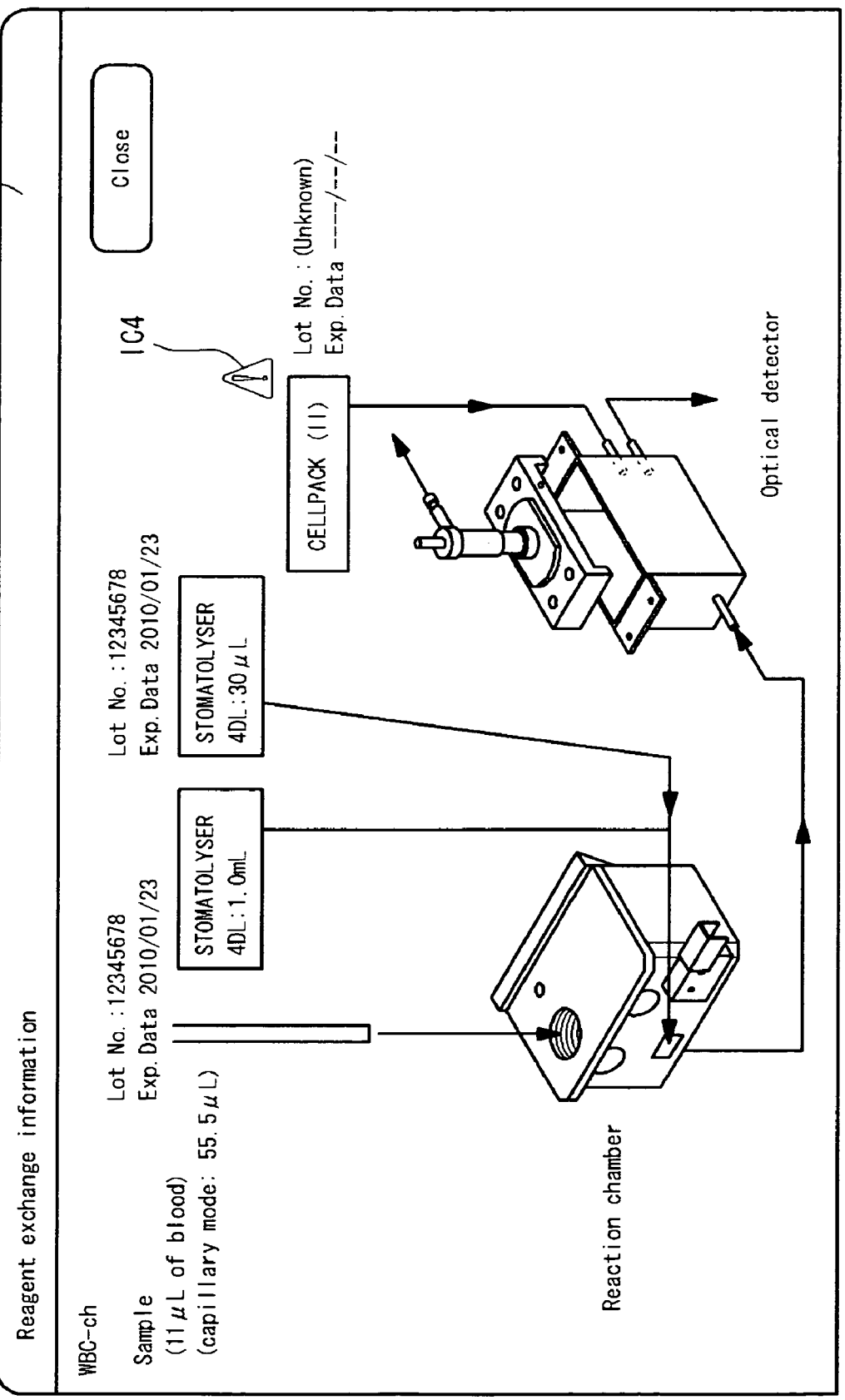
FIG. 26 illustrates a reagent information screen displayed in the data processing apparatus of the hemocytometer of FIG. 1.

In FIG. 16, Step S124 determines whether the display of the reagent information screen is instructed or not. When the display of the reagent information screen is instructed, Step S125 allows the reagent information screen to be displayed in the display 32. Specifically, when the user clicks the note SC2c as reliability information shown in FIG. 22 or the warning marks IC1a to IC3c shown in FIG. 23 to FIG. 25, then a reagent information screen SC6 as shown in FIG. 26 is displayed. This reagent information screen SC6 displays a genuine product name, the lot No., and the expiration date of a to-be-used reagent used in a predetermined measurement item (WBC in this case) as well as a graphic showing a portion to which the reagent is supplied (reaction chamber or detector). With regard to a reagent not using a genuine product, the warning mark IC4 showing reliability information is put and "unknown" or a blank space is displayed in display columns for displaying the lot No. and expiration date. Thus, the user can instantly recognize, upon seeing the reagent information screen SC6, reagent supplied to which portion is a not-genuine product.

Another example of the reagent information screen is shown in FIG. 27 in which the analysis result display screen SC2 includes a reagent information tab SC2d. The user can select this tab SC2d to display a reagent information screen SC2e. This reagent information screen SC2e displays the name, the lot No. and expiration date of a reagent that is a genuine product. With regards to a reagent not using a genuine product, "unknown" or a blank space is displayed in display columns for displaying the lot No. and expiration date and a text display is displayed to show the information showing that the analysis result cannot be guaranteed for any measurement item using the reagent together with a warning mark IC5 as reliability information. Thus, the user can recognize, upon seeing this reagent information screen SC2e, which reagent is a not-genuine product and a measurement item that leads to an analysis result having a low reliability.

Figure 28:
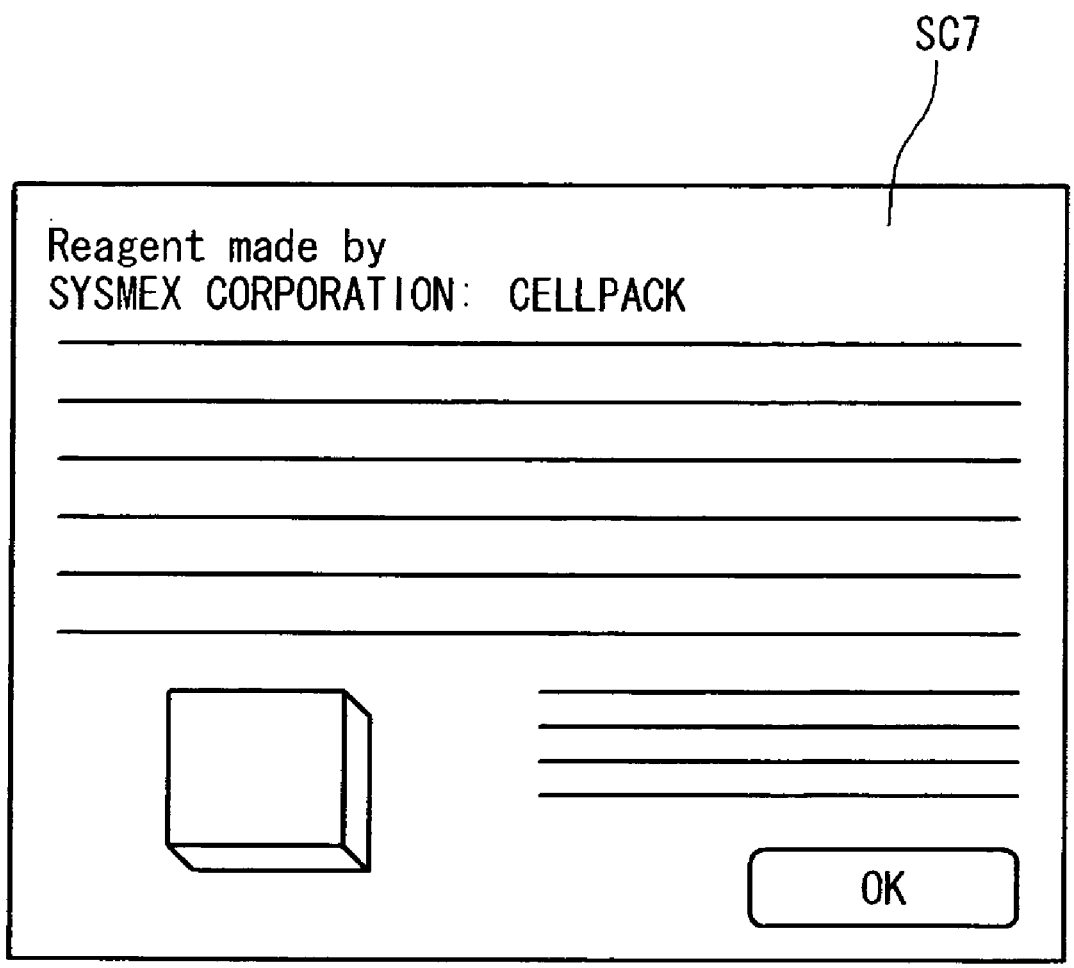
FIG. 28 illustrates the reagent information screen displayed in the data processing apparatus of the hemocytometer of FIG. 1.

As another example of reagent information screen, the note SC2c as reliability information shown in FIG. 22 and the warning marks IC1a to IC3c of FIG. 23 to FIG. 25 can be also clicked by the user to display a reagent information screen SC7 as shown in FIG. 28. This reagent information screen SC7 displays a text display of the information regarding a reagent of a genuine product (e.g., performance and advantage of the genuine product and how to obtain the product). By seeing the display of such information, the user can recognize the priority and significance of the use of a genuine product and can smoothly obtain the genuine product.

Step S126 of FIG. 16 determines whether a printing operation of the analysis result is instructed or not. A print instruction is issued when the user clicks print button (print icon) IC6 provided in tool bars in the analysis result display screens SC1 and SC2 as shown in FIG. 21 and FIG. 22. When a print instruction is issued, then the processing proceeds to Step S127 to allow the printer 4 to print the analysis result on a paper.

Figure 20:
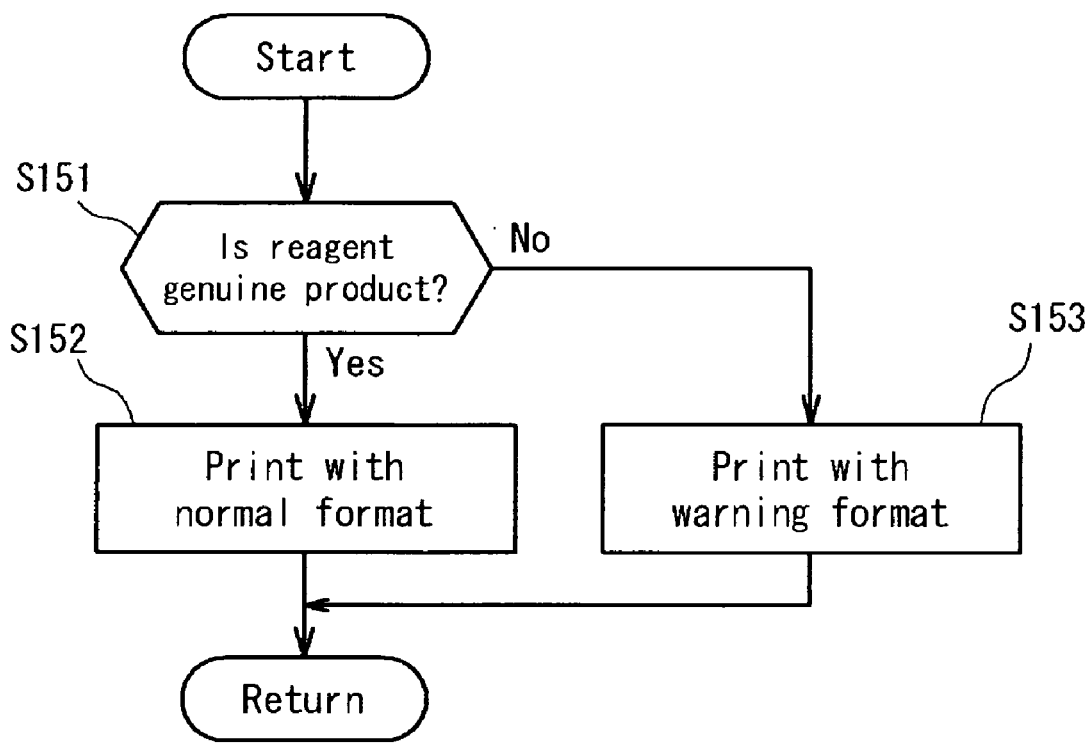
FIG. 20 is a flowchart illustrating an analysis result print control in the hemocytometer of FIG. 1.

FIG. 20 is a flowchart illustrating the control of the printing of the analysis result. Step S151 determines whether the reagent being used is a genuine product or not. This determination is performed based on the check result checked in Step S112 in the operation at the startup shown in FIG. 14. When the reagent is a genuine product, then Step S152 allows the analysis result to be printed with a normal format. Thereafter, the processing proceeds to Step S128 of FIG. 16. When the reagent is a not-genuine product, Step S153 allows the analysis result to be printed with a format including a warning message.

Figure 29:
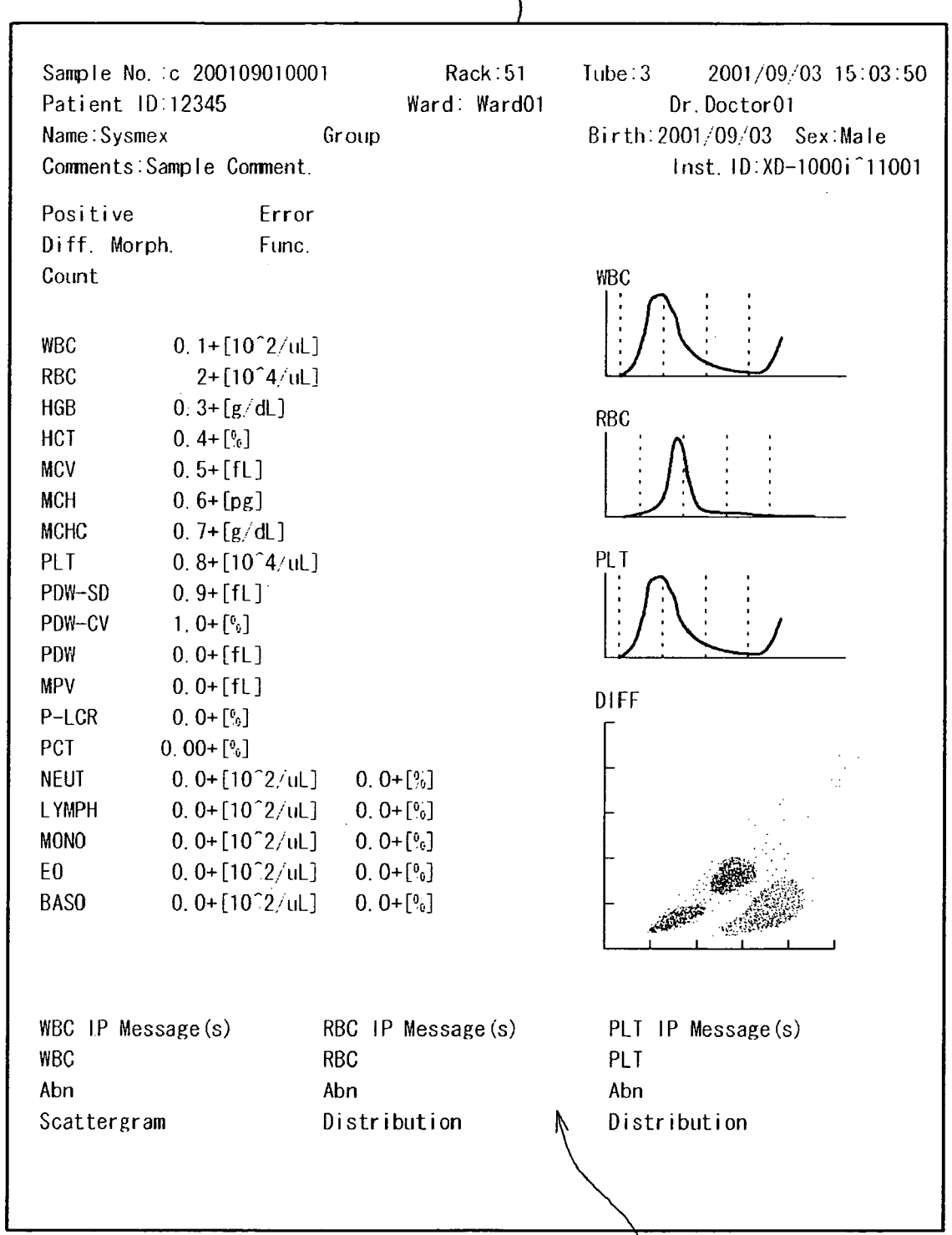
FIG. 29 illustrates an example of an analysis result printed by the printer of the hemocytometer of FIG. 1 when not-genuine reagent is used.

FIG. 29 illustrates an analysis result printed with a format including a warning message. In FIG. 29, various information regarding an examination (e.g., a measurement item name, numerical data, a scattergram) is printed on a paper S. This information is printed so that the reliability information Sa is superposed on the information and the reliability information Sa is printed as a background print. The reliability information Sa shows that reagent is a not-genuine product and the supplier of the hemocytometer 1 cannot guarantee the analysis result. Thus, the user can securely recognize the analysis result and the reliability information without missing the information. Furthermore, a situation can be also prevented where reliability information Sa is cut off when the printed analysis result including the reliability information Sa is presented to a patient or the outside for example.

An analysis result can be also printed so as to include the reliability information shown in FIG. 23 to FIG. 25 (warning marks IC1a to IC3c) that corresponds to the display of a measurement item name, numerical data, or a scattergram for example. Alternatively, instead of displaying both of the analysis result and the warning on one sheet as shown in FIG. 29, the analysis result and the warning may be also printed on different papers.

Step S128 of FIG. 16 determines whether the instruction to complete the screen display is issued or not. When the instruction is issued, then the operation is completed. When the instruction is not issued, the processing returns to Step S124.

As described above, the hemocytometer 1 according to this embodiment determines whether the reagent is appropriate for the measurement of a sample by the measurement section 2 or not based on the Reagent Code 60a received by the reagent exchange screen SC3. Based on the determination result, the analysis result and the reliability information showing that the analysis result has a low reliability are outputted together. Thus, the user can recognize not only the analysis result but also the reliability of the analysis result. This can avoid a situation where a patient is subjected to an inappropriate treatment or medication based on the analysis result having a low reliability.

Also according to this embodiment, when the reagent is determined to be a nondedicated reagent (not-genuine product) that is not appropriate for the analysis, the display 32 displays the warning screen SC5 at the startup of the hemocytometer 1. This allows the user to recognize, prior to carrying out the analysis, that the analysis result has a low reliability.

Also according to this embodiment, whether the reagent is a dedicated reagent (genuine product) appropriate for the sample analysis by the measurement section 2 or not is determined based on both of the information for the Reagent Code 60a and the information for the reagent remaining amount received by the reagent exchange screen SC3. Thus, the determination regarding whether the reagent is a dedicated reagent (genuine product) or not can be performed accurately.

Second Embodiment

Figure 30:
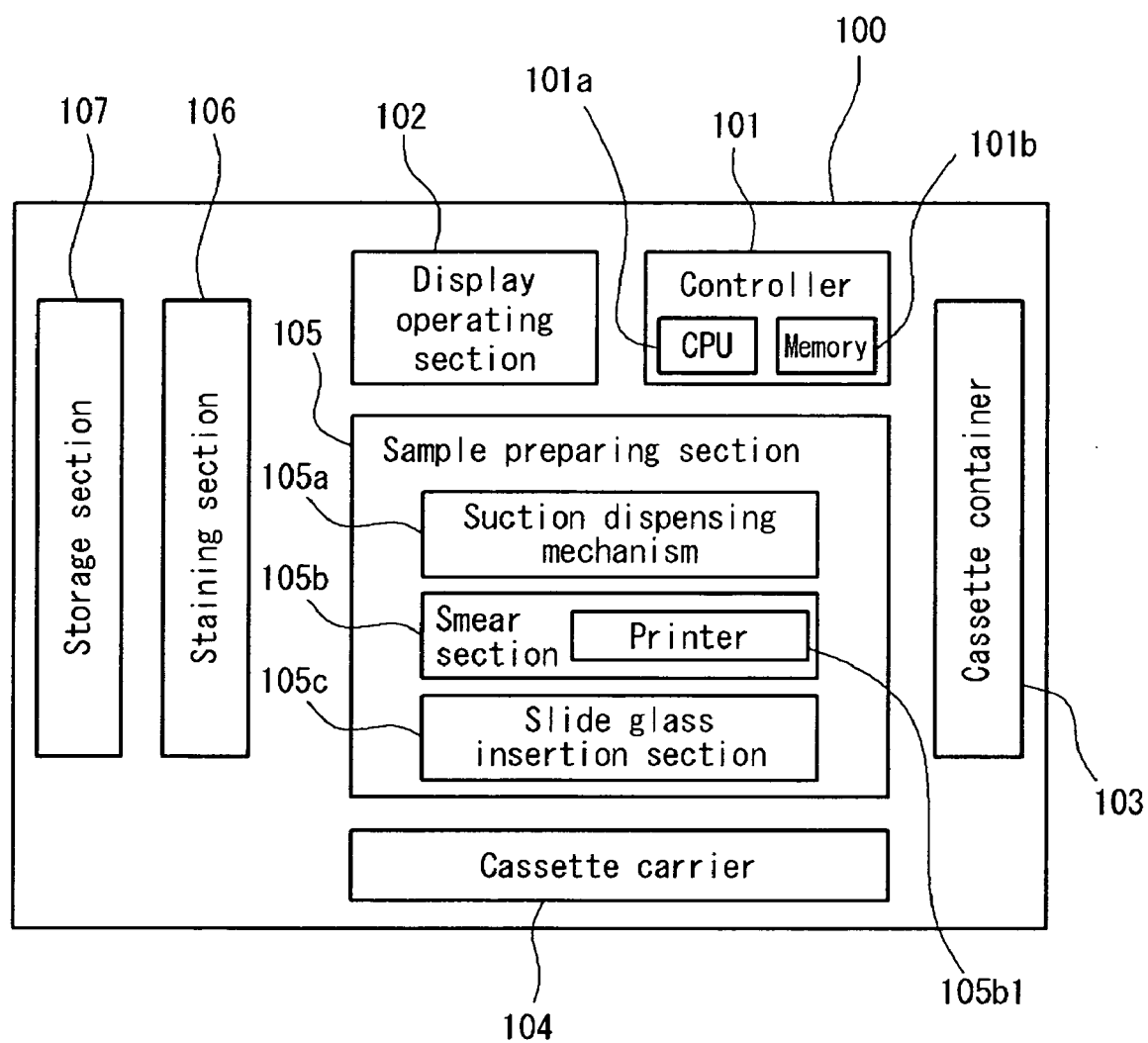
FIG. 30 is a block diagram illustrating the configuration of a smear preparing apparatus according to a second embodiment of the present invention.

FIG. 30 is a block diagram illustrating the configuration of a smear preparing apparatus 100 that is a sample processing apparatus according to the second embodiment of the present invention. The smear preparing apparatus 100 is provided adjacent to the above-described hemocytometer 1 for example. The smear preparing apparatus 100 prepares, based on the analysis result by the hemocytometer 1, a smear to a sample requiring a reexamination using a smear. The smear is also prepared by reagent such as stain solution, diluent or the like.

The smear preparing apparatus 100 includes: a controller 101, a display operating section 102, a cassette container 103, a cassette carrier 104, a sample preparing section 105, a staining section 106, and a storage section 107. The controller 101 is composed of a CPU 101a and a memory 101b such as ROM or RAM for example. The controller 101 has a function to control the operation of the smear preparing apparatus 100. The display operating section 102 is composed of a touch panel through which various settings for the smear preparing apparatus 100 can be inputted and the status can be displayed for example.

The cassette container 103 stores therein a cassette (not shown) that can accommodate a slide glass 110 (see FIG. 31) and stain solution for a staining process. The cassette container 103 has a function to send the cassette to the cassette carrier 104. The cassette carrier 104 has a function to carry the cassette received from the cassette container 103 to the sample preparing section 105 and the staining section 106.

Figure 31:
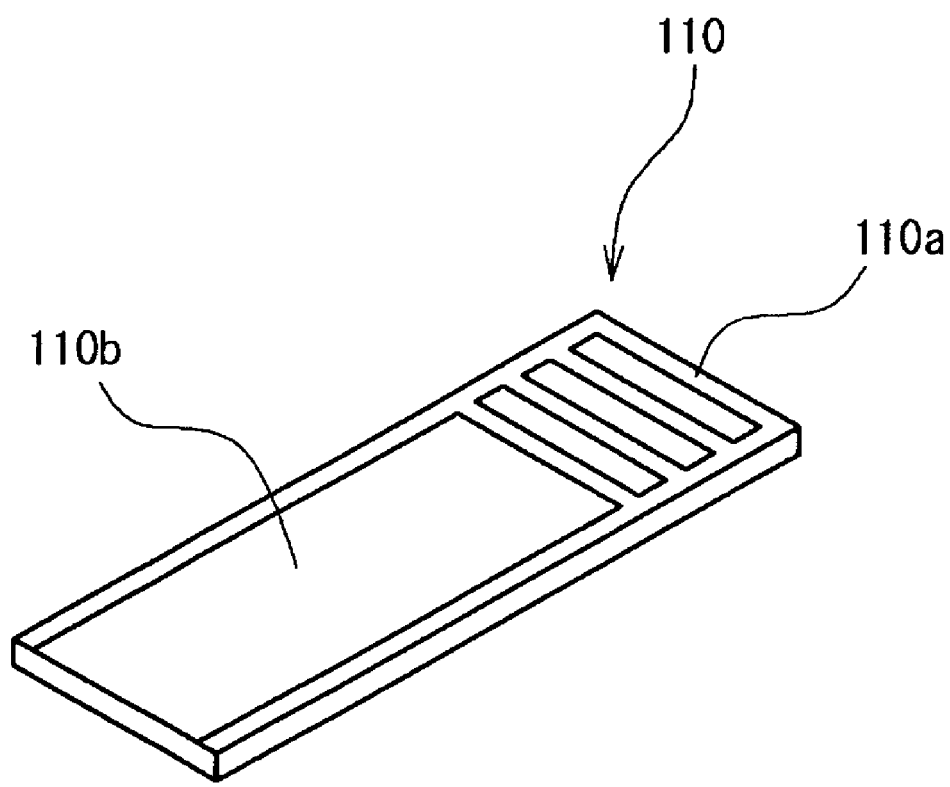
FIG. 31 is a perspective view illustrating a slide glass used in the smear preparing apparatus of FIG. 30.

The sample preparing section 105 includes: a suction dispensing mechanism 105a; a smear section 105b; and a slide glass insertion section 105c. The suction dispensing mechanism 105a has a function to suck the blood in a blood collection tube automatically supplied from a carrying apparatus (not shown) or a manually supplied blood collection tube to drip the blood onto the slide glass 110. The smear section 105b has a function to smear the blood dripped on the slide glass 110 to dry the blood to allow a printer 105b1 to print smear-related information. The slide glass 110 includes, as shown in FIG. 31, a sample preparing region 110b and a frost section (information display region) 110a provided at one side of the sample preparing region 110b. The printer 105b1 prints the smear-related information to this frost section 110a.

As shown in FIG. 30, the slide glass insertion section 105c has a function to insert the slide glass 110 smeared with the sample to the cassette sent from the cassette carrier 104. The slide glass 110 inserted into the cassette is carried by the cassette carrier 104 to the staining section 106.

The staining section 106 supplies stain solution (reagent) to the cassette sent from the cassette carrier 104 to stain the slide glass 110 smeared with the sample. The storage section 107 has a function to store a cassette accommodating the slide glass 110 stained by the staining section 106. The stained slide glass 110 stored in this storage section 107 is subjected to an analysis by a visual inspection for example. In this manner, the smear preparing apparatus 100 prepares a smear as a processing result by processing the blood by the reagent as described above. The prepared smear is taken out by the user of the smear preparing apparatus 100 or a carrying mechanism (not shown) to the outside of the apparatus.

As shown in FIG. 31, the smear-related information such as a date, a patient name, or a sample No. can be printed on the frost section 110a of the slide glass 110. The printer 105b1 is configured to print the reliability information on the frost section 110a with regard to a smear prepared using a reagent of a not-genuine product. The determination regarding whether the reagent is a genuine product or not and the control for printing the reliability information are performed by the CPU 101a of the controller 101 in the same manner as in the first embodiment.

Figure 32A:
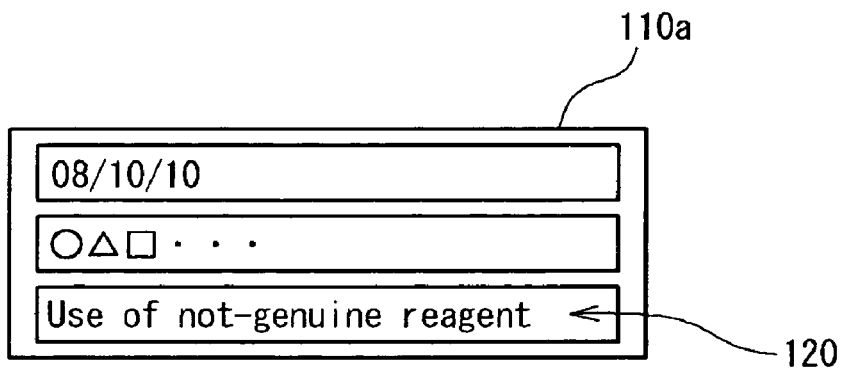
FIG. 32 illustrates reliability information printed by the smear preparing apparatus of FIG. 30.
Figure 32B:
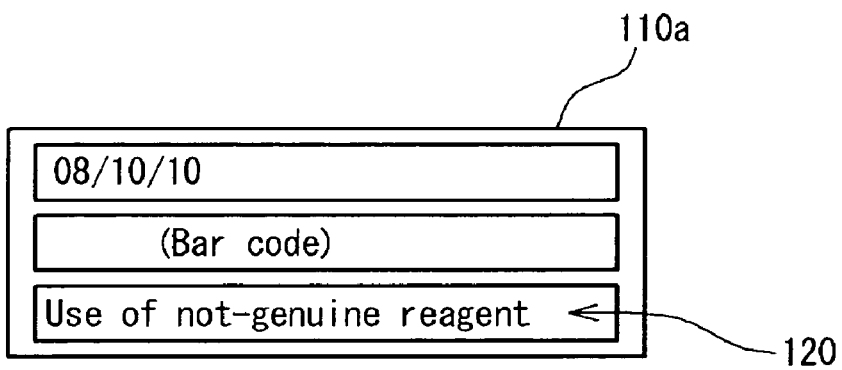
Figure 32C:
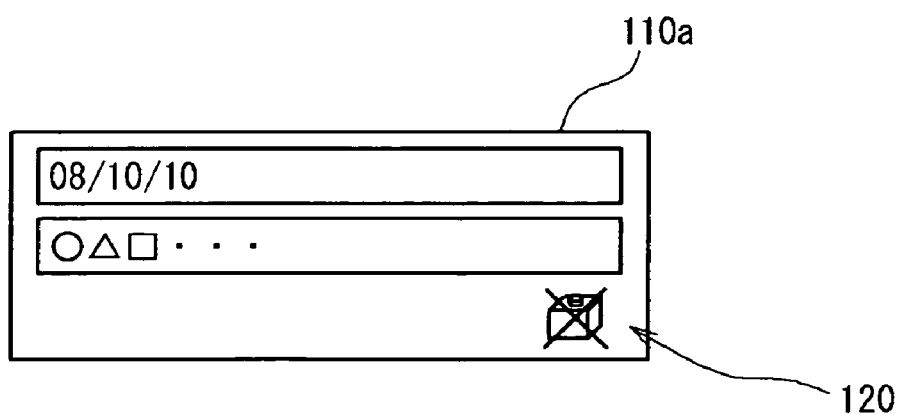

FIGS. 32(a) to 32(c) illustrate an example of a print of the reliability information. In FIG. 32(a), texts can be printed in three lines in the frost section 110a so that the first line includes a date, the second line includes a sample No. or the like, and the third line includes reliability information 120 showing that "a not-genuine reagent is used" for example.

In FIG. 32(b), texts can be printed on the uppermost part and the lowermost part of the frost section 110a and a one-dimensional bar code can be printed on the center. The reliability information 120 showing that "a not-genuine reagent is used" is printed in the upper or lower line of the bar code. The bar code may be also a two-dimensional bar code.

In FIG. 32(c), three lines are printable in the frost section 110a as in those shown in FIG. 32(a). However, an image of "×" mark is printed over a reagent container graphic that is different depending on the type of the reagent as the reliability information 120. Through this image, the user can recognize that the reagent is not a genuine product and which reagent is a not-genuine product. In the examples shown in FIGS. 32(a) and 32(b), the type of the reagent using a not-genuine product can be also printed by a text or a graphic.

The respective embodiments disclosed herein are the illustrative ones in all respects and should be interpreted as the not limitative ones. The scope of the present invention is not defined by the above-described description of the embodiments but is defined by the claims and includes all modifications within the intention and scope equivalent to the claims.

For example, although the above-described embodiments have described an example in which the present invention is applied to the hemocytometer 1 and the smear preparing apparatus 100 as the sample processing apparatus, the invention is not limited to this. The invention can be also used to other medical sample processing apparatuses such as a blood coagulation analyzer, an immunity analyzer, a urine visible component analyzer so long as the sample processing apparatus uses dedicated reagent to process a sample.

In the first embodiment, an example of the configuration has been shown in which the warning screen is displayed at the startup. However, the present invention is not limited to this. A warning screen may be also displayed whenever the analysis result display screen is displayed.

In the above embodiment, a configuration has been shown to determine whether the reagent is a dedicated reagent (genuine product) or a nondedicated reagent (not-genuine product). However, the present invention is not limited to this. Another configuration may be also used that includes not only the determination regarding whether the reagent is a dedicated reagent or not but also a determination to determine whether the reagent has an expired expiration date or not by comparing the expiration date of the reagent with a measurement date. When the reagent does not have an expired expiration date, a normal screen display or a normal print is performed. When the reagent has an expired expiration date, reliability information showing that the reagent has an expired expiration date can be displayed or printed.

In the above embodiment, a configuration has been shown to determine whether the reagent is a dedicated reagent (genuine product) or a nondedicated reagent (not-genuine product). However, the present invention is not limited to this. Another configuration may be also used in which another auxiliary item used to process a sample can be determined with regard to whether the auxiliary item is a genuine product or a not-genuine product. When the substance is a not-genuine product, the reliability information is outputted. For example, the slide glass 110 used in the second embodiment can be determined with regard to whether the slide glass 110 is a genuine product or a not-genuine product. When the slide glass 110 is a not-genuine product, the reliability information is outputted. Still another configuration can be also used in which a disposable cuvette for storing a sample that is used for an optical measurement by a blood coagulation analyzer, an immune measurement apparatus, or a biochemical measurement apparatus for example is determined with regard to whether the cuvette is a genuine product or a not-genuine product. When the cuvette is a not-genuine product, the reliability information is outputted. Still another configuration can be also used in which a disposable dispensing pippet for sucking a sample or a reagent that is used in a blood coagulation analyzer, an immune measurement apparatus, or a biochemical measurement apparatus for example is determined with regard to whether the dispensing pipette is a genuine product or a not-genuine product. When the dispensing pipette is a not-genuine product, the reliability information is outputted.

The invention claimed is:

1. A sample processing apparatus, comprising:
a sample processing unit for processing a biological or chemical sample with an auxiliary item used to process the sample;
an output device for outputting a processing result by the sample processing unit; and
a controller configured for
receiving identifying information associated with the auxiliary item,
evaluating the received identifying information against stored identifying information associated with at least one other auxiliary item historically used with the sample processing unit,
confirming, when the received identifying information is the same as the stored identifying information, whether or not any past amount of the at least one other auxiliary item historically used with the sample processing unit remains in the sample processing unit,
determining, when the received identifying information is the same as the stored identifying information and a past amount of the at least one other auxiliary item historically used with the sample processing unit does not remain in the sample processing unit, that the auxiliary item is not appropriate for sample processing by the sample processing unit,
determining, when the received identifying information is the same as the stored identifying information and a past amount of the at least one other auxiliary item historically used with the sample processing unit does remain in the sample processing unit, that the auxiliary item is appropriate for sample processing by the sample processing unit, and
controlling, when determining that the auxiliary item is not appropriate for the sample processing by the sample processing unit, the output device so as to output the processing result and reliability information showing that the processing result has a low reliability.

2. The sample processing apparatus according to claim 1, wherein the auxiliary item is a reagent.

3. The sample processing apparatus according to claim 2, wherein the sample processing unit is a sample analyzing unit that analyzes the sample with regard to a plurality of analysis items to obtain analysis results, and
the controller determines whether or not the reagent is appropriate for the sample analysis by the sample analyzing unit, and controls, when determining that the reagent is not appropriate for the sample analysis by the sample analyzing unit, the output device so as to output the analysis results and the reliability information.

4. The sample processing apparatus according to claim 3, wherein the controller determines, with regard to the respective plurality of analysis items, whether or not the reagent is appropriate for the sample analysis by the sample analyzing unit, and controls, when determining that the reagent is not appropriate for the sample analysis by the sample analyzing unit, the output device so as to output the analysis results and the reliability information with identifying analysis item.

5. The sample processing apparatus according to claim 1, wherein the output device comprises a printer for printing the processing result, and
the controller controls the printer so as to print the processing result and the reliability information.

6. The sample processing apparatus according to claim 5, wherein the controller controls the printer so as to superimposingly print the reliability information on the processing result.

7. The sample processing apparatus according to claim 2, wherein the sample processing unit is configured to process the sample with a plurality of reagents,
the controller determines whether or not the respective plurality of reagents are appropriate for the sample processing by the sample processing unit, and controls, when determining that at least one of the plurality of reagents is not appropriate for the processing by the sample processing unit, the output device so as to output the processing result and the information identifying the reagent determined as inappropriate for the processing.

8. The sample processing apparatus according to claim 1, wherein the controller controls the output device so as to further output information regarding the auxiliary item used for the sample processing.

9. The sample processing apparatus according to claim 1, wherein the controller determines whether or not the auxiliary item is a genuine product and controls, when determining that the auxiliary item is not a genuine product, the output device so as to output the processing result and the reliability information.

10. The sample processing apparatus according to claim 1, wherein the reliability information includes information showing that the processing result cannot be guaranteed.

11. The sample processing apparatus according to claim 1, wherein the sample processing unit is a smear preparing apparatus that smears a sample over a slide glass to prepare a smear,
the processing result is the smear,
the output device comprises a printer, and
the controller controls the printer so as to print the reliability information on the slide glass.

12. The sample processing apparatus according to claim 1, wherein the sample processing unit is a sample analyzing unit that analyzes the sample using a cuvette storing the sample, and
the auxiliary item is the cuvette, and
the controller determines whether or not the cuvette is a genuine product and controls, when determining that the cuvette is not a genuine product, the output device so as to output the processing result and the reliability information.

13. The sample processing apparatus according to claim 12,
wherein the sample analyzing unit is selected from a group consisting of a blood coagulation analyzer, an immune measurement apparatus, and a biochemical measurement apparatus.

14. The sample processing apparatus according to claim 1, wherein the sample processing unit is a measurement apparatus that analyzes the sample using a disposable dispensing pipette for sucking the sample or a reagent,
the auxiliary item is the disposable dispensing pipette, and
the controller determines whether or not the disposable dispensing pipette is a genuine product and controls, when determining that the disposable dispensing pipette is not a genuine product, the control device so as to output the processing result and the reliability information.

15. A processing result output method by a sample processing apparatus, comprising:
receiving identifying information associated with an auxiliary item used to process a biological or chemical sample;
processing the sample with using the auxiliary item;
acquiring a processing result of the sample processed using the auxiliary item;
evaluating the received identifying information against stored identifying information associated with at least one other auxiliary item historically used with the sample processing unit;
confirming, when the received identifying information is the same as the stored identifying information, whether or not any past amount of the at least one other auxiliary item historically used with the sample processing unit remains in the sample processing unit;
determining, when the received identifying information is the same as the stored identifying information and a past amount of the at least one other auxiliary item historically used with the sample processing unit does not remain in the sample processing unit, that the auxiliary item is not appropriate for sample processing by the sample processing unit;
determining, when the received identifying information is the same as the stored identifying information and a past amount of the at least one other auxiliary item historically used with the sample processing unit does remain in the sample processing unit, that the auxiliary item is appropriate for sample processing; and
outputting, when the auxiliary item is determined as inappropriate for the sample processing, the processing result and reliability information showing that the processing result has a low reliability.

16. The output method according to claim 15,
wherein the processing step comprises a step of using reagent as the auxiliary item to prepare the sample,
the acquisition step comprises a step of acquiring an analysis result of the sample prepared in the preparation step, and
the output step comprises a step of outputting, when the reagent is determined as inappropriate for the sample processing, the analysis result and the reliability information.

17. The output method according to claim 15,
wherein the processing step comprises a step of smearing a sample over a slide glass to stain the sample by stain solution as the auxiliary item,
the acquisition step comprises a step of taking out the smear stained by the stain solution from a smear preparing apparatus, and
the output step comprises a step of printing the reliability information on the slide glass when the stain solution is determined as inappropriate for staining the sample.

18. The output method according to claim 15,
wherein the processing step comprises a step of analyzing a sample using a cuvette as the auxiliary item,
the acquisition step comprises a step of acquiring an analysis result of the sample measured in the measurement step, and
the output step comprises a step of outputting the analysis result and the reliability information when the cuvette is determined as inappropriate for measuring the sample.

19. The output method according to claim 15,
wherein the processing step comprises a step of using a disposable dispensing pipette as the auxiliary item to suck the sample,
the acquisition step comprises a step of acquiring an analysis result of the sample sucked in the suction step, and
the output step comprises a step of outputting the analysis result and the reliability information when the disposable dispensing pipette is determined as inappropriate for sucking the sample.

20. A computer program product, comprising:
a computer readable medium; and
instructions, on the computer readable medium, adapted to enable a general purpose computer to perform operations, comprising:
receiving identifying information associated with an auxiliary item used to process a biological or chemical sample,
acquiring a result of a processing of a sample processed with an auxiliary item;
evaluating the received identifying information against stored identifying information associated with at least one other auxiliary item historically used with the sample processing unit,
confirming, when the received identifying information is the same as the stored identifying information, whether or not any past amount of the at least one other auxiliary item historically used with the sample processing unit remains in the sample processing unit,
determining, when the received identifying information is the same as the stored identifying information and a past amount of the at least one other auxiliary item historically used with the sample processing unit does not remain in the sample processing unit, that the auxiliary item is not appropriate for sample processing by the sample processing unit, determining, when the received identifying information is the same as the stored identifying information and a past amount of the at least one other auxiliary item historically used with the sample processing unit does remain in the sample processing unit, that the auxiliary item is appropriate for sample processing, and outputting, when the auxiliary item is determined as inappropriate for the sample processing, the processing result and reliability information showing that the processing result has a low reliability.

\* \* \* \* \*